US011890302B2

(12) United States Patent
Patakas et al.

(10) Patent No.: US 11,890,302 B2
(45) Date of Patent: Feb. 6, 2024

(54) GAMMA DELTA CAR-T CELLS COMPRISING FC GAMMA INTRACELLULAR SIGNALING DOMAINS

(71) Applicant: TC Biopharm Limited, Holytown Motherwell (GB)

(72) Inventors: Agapitos Patakas, Holytown Motherwell (GB); Timothy London, Holytown Motherwell (GB); Emilio Cosimo, Holytown Motherwell (GB)

(73) Assignee: TC BIOPHARM LIMITED, Holytown Motherwell (GB)

( * ) Notice: Subject to any disclaimer, the term of this patent is extended or adjusted under 35 U.S.C. 154(b) by 559 days.

(21) Appl. No.: 16/649,982

(22) PCT Filed: Oct. 1, 2018

(86) PCT No.: PCT/GB2018/052801
§ 371 (c)(1),
(2) Date: Mar. 24, 2020

(87) PCT Pub. No.: WO2019/064030
PCT Pub. Date: Apr. 4, 2019

(65) Prior Publication Data
US 2020/0289564 A1 Sep. 17, 2020

(30) Foreign Application Priority Data
Sep. 29, 2017 (GB) .................... 1715918

(51) Int. Cl.
*A61K 35/17* (2015.01)
*C07K 14/735* (2006.01)
*C12N 15/86* (2006.01)

(52) U.S. Cl.
CPC ........ *A61K 35/17* (2013.01); *C07K 14/70535* (2013.01); *C12N 15/86* (2013.01); *C07K 2319/03* (2013.01); *C12N 2740/15043* (2013.01)

(58) Field of Classification Search
CPC ... A61K 35/17; C07K 14/70535; C12N 15/86
See application file for complete search history.

(56) References Cited

FOREIGN PATENT DOCUMENTS

| EP | 3 300 745 B1 | 9/2019 |
|---|---|---|
| JP | 2016-508518 A | 3/2016 |
| WO | WO 2014/127261 A1 | 8/2014 |
| WO | WO 2014/145252 A2 | 9/2014 |
| WO | WO 2016/044605 A1 | 3/2016 |
| WO | WO 2016/097231 A2 | 6/2016 |
| WO | WO 2016/174461 A1 | 11/2016 |
| WO | WO 2017/041106 A1 | 3/2017 |
| WO | WO 2017/140632 A1 | 8/2017 |

OTHER PUBLICATIONS

Van der Heijden et al., Phenotypical variations in IgG receptors by nonclassical FCGR2C alleles. J. Immunol. 188, 1318-1324, 2012. (Year: 2012).*
Smith, et al., "FcγRIIB in autoimmunity and infection: evolutionary and therapeutic implications," Nature Reviews Immunology, 10(5):328-343, (2010).
International Search Report and Written Opinion for International Application No. PCT/GB2018/052801 dated Dec. 14, 2018, 16 pages.

* cited by examiner

Primary Examiner — Elly-Gerald Stoica
(74) Attorney, Agent, or Firm — Alston & Bird LLP

(57) ABSTRACT

The present invention relates to gamma delta (γδ) T cells and/or Natural Killer (NK) cells expressing constructs to provide for the expression of a Chimeric Antigen Receptor (CAR) incorporating the signalling domain of FCY Receptors. Suitably the invention also relates to constructs to provide such CARs and methods for introducing such CARs into cells and expressing such CARs in cells comprising receptors of gamma delta (γδ) T cells and/or Natural Killer (NK) cells.

7 Claims, 8 Drawing Sheets

Specification includes a Sequence Listing.

Figure 2:
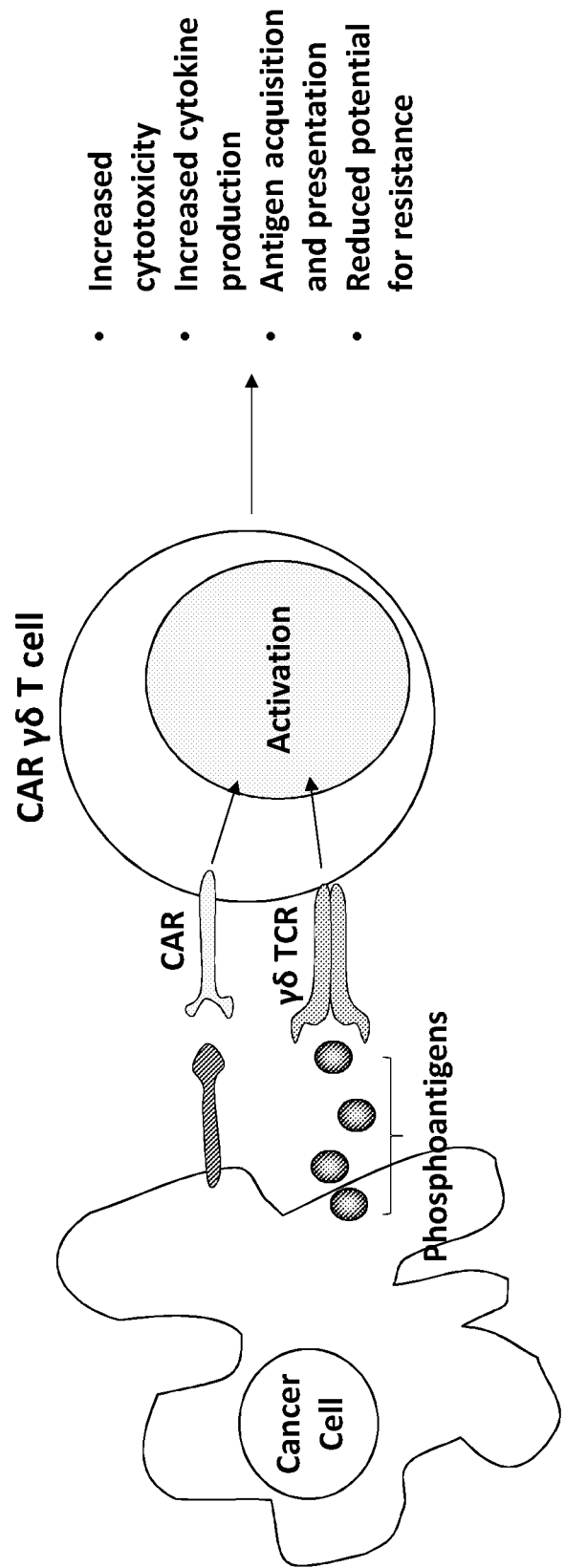

Figure 2. Mode of action of the CARs in γδ T cells

Figure 3:
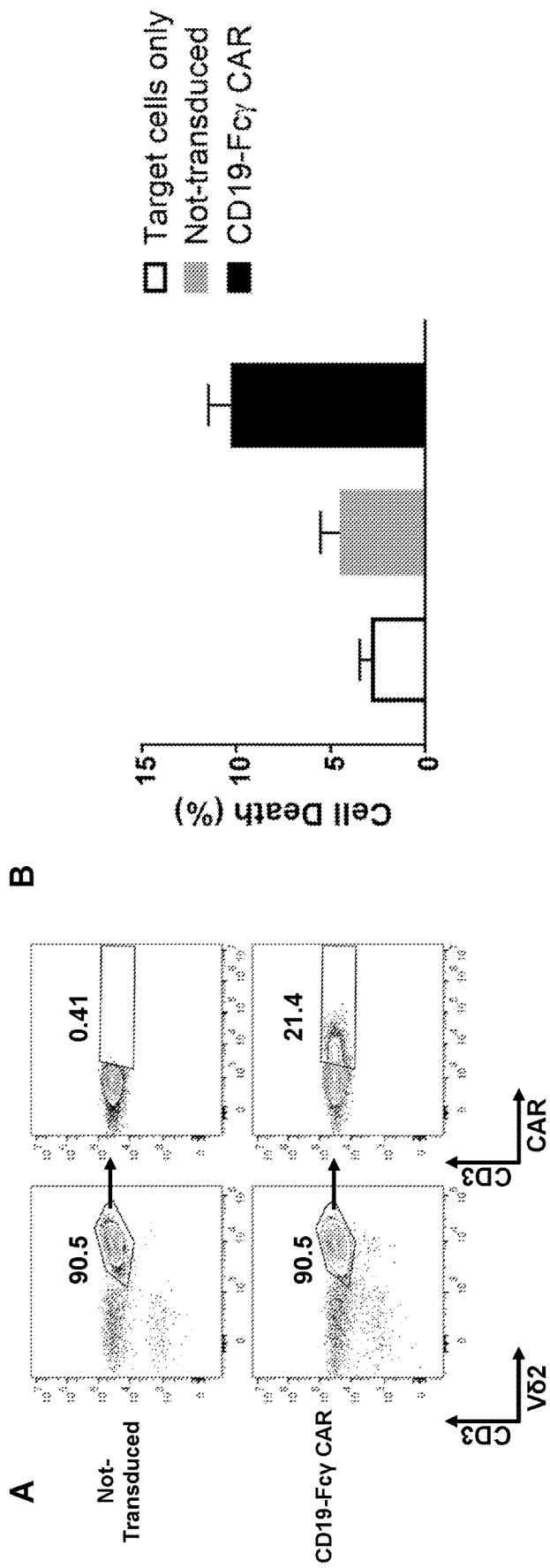

Figure 3. Increase cytotoxic potential of CAR-expressing gamma delta T cells

GAMMA DELTA CAR-T CELLS COMPRISING FC GAMMA INTRACELLULAR SIGNALING DOMAINS

CROSS-REFERENCE TO RELATED APPLICATIONS

This application is a national stage entry of PCT/GB2018/052801 filed Oct. 1, 2018, which claims the benefit of GB Application No. 1715918.7, filed Sep. 29, 2017, herein incorporated by reference in its entirety for all purposes.

REFERENCE TO A SEQUENCE LISTING SUBMITTED AS A TEXT FILE VIA EFS WEB

The Sequence Listing written in file 545879SEQL-ST.TXT is 28,936 bytes, was created on Mar. 23, 2020, and is hereby incorporated by reference.

FIELD OF THE INVENTION

The present invention relates to gamma delta (γδ) T cells and/or Natural Killer (NK) cells expressing constructs to provide for the expression of a Chimeric Antigen Receptor (CAR) incorporating the signalling domain of Fcγ Receptors. Suitably the invention also relates to constructs to provide such CARs and methods for introducing such CARs into cells and expressing such CARs in cells comprising receptors of gamma delta (γδ) T cells and/or Natural Killer (NK) cells.

BACKGROUND

Cellular receptors for immunoglobulins (Ig) (Fc-receptors) were identified four decades ago and play a central role in the initiation and resolution of the immune response. These receptors set thresholds for the activation of B cells, regulate the maturation of dendritic cells and couple the specificity of antibody responses to innate effector functions, such as phagocytosis and antibody dependent cell-mediated cytotoxicity (ADCC). In all mammalian species studied to date, four different classes of Fc receptors (FcR) that recognise IgG have been identified, FcγRI (CD64), FcγRII (CD32), FcγRIII (CD16) and FcγRIV. Based on their function they can be subdivided into two classes, the activation and inhibitory receptors, which transmit signals via immunoreceptor tyrosine based activation (ITAM) or inhibitory motifs (ITIM) respectively. FcγRIIB belongs to a family of immune inhibitory receptors which include CTLA-4 and PD-1 that regulate immune responses. Activating FcγRs include FcγRI, FcγRIIA, FcγRIII and FcγRIV. Engagement of activating Fcγ receptors triggers many biological functions, such as the proliferation of B cells, phagocytosis by macrophages, cytolysis, degranulation and transcriptional activation of cytokine encoding genes, which initiate inflammatory responses. Most of the activating type FcRs associate with the Fc receptor common γ chain (FcRγ), which contains an ITAM (the FcRγ chain (FcR common γ chain)) is different from the common γ chain (CD132) used by cytokine receptors). On the other hand, the activation receptors CD32a and CD32c have intracellular ITAM containing domains. Aggregation of Fc receptor after ligand binding results in ITAM phosphorylation and activation of the cells.

Immune cells such as gamma delta T cells and NK cells express Fcγ receptors that mediate at least part of their function. These cells are part of the innate immune system and are indispensable for immunity against cancer and infections. They utilise a number of receptors to identify and kill infected and cancerous cells. One of the ways they mediate their cytotoxic activity is through Fcγ receptors by antibody dependent cell cytotoxicity (ADCC). This is an immune mechanism whereby an effector cell of the immune system actively lyses a target cell, to which membrane surface antigens on the target cell have been bound by specific antibodies. Gamma delta T cells and NK cells express Fcγ receptors CD32 and CD16 that mediate ADCC. Both of these cell types have been trialled as cell therapies against various types of cancer (e.g. melanoma, renal cell carcinoma etc) demonstrating safety and therapeutic potential. In vitro studies have demonstrated that the effector functions of these cells can be potentiated by monoclonal antibodies presumably due to activation signals initiated by the expressed FcRs. This has led to the suggestion that these cell therapies should be combined with monoclonal antibody therapies e.g. Trastuzumab that targets the HER2 receptor. In this way, the activity of these cells will be focused to the cell bound by the antibody (Tokuyama et al, International journal of Cancer, 2011, Vγ9Vδ2 T cell cytotoxicity against tumor cells is enhanced by monoclonal antibody drugs—Rituximab and trastuzumab and Gertner-Dardenne et al, Blood, 2009, Bromohydrin pyrophosphate enhances antibody-dependent cell-mediated cytotoxicity induced by therapeutic antibodies).

Chimeric Antigen Receptors (CARs)

A very effective way to redirect and target the activity of the immune system against specified targets is by the expression of Chimeric Antigen Receptors (CARs) on a cell of the immune system. CARs are modular proteins which graft the specificity of a monoclonal antibody (mAb) to the effector function of an immune cell. Their usual form is that of a type I transmembrane domain protein with an antigen recognizing amino terminus, a spacer, and a transmembrane domain which are connected to a signalling endodomain which transmits survival and activation signals.

The CAR may be a fusion of single-chain variable fragments (scFv) derived from monoclonal antibodies which recognize a target antigen, fused via a spacer and a transmembrane domain to the signalling endodomain. Originally, they were developed to redirect the immune function of alpha beta T cells against cancer cells that express the targeted antigen. This was due to the inability of identifying and expanding cancer specific alpha beta T cell clones for use in clinical trials due to their rarity in the peripheral blood or biopsies. The choice of signalling domains used in such CARs reflects the development of CAR in alpha beta T cells. Most CARs usually include signalling domains from the CD3zeta (ζ) chain, which provides T cell receptor-like (signal 1) stimulation and domains from CD28 or CD137 that provide co-stimulation (signal 2). Upon recognition of the target antigen by the CAR, T cell activation ensues that results in direct cytotoxicity to the cell expressing the antigen. Even though impressive responses have been reported in trials employing alpha beta T cells expressing CARs, these were always accompanied by serious adverse events, such as cytokine release syndrome (CRS), neurotoxicity and in many cases death. This has been in one degree attributed to the uncontrolled activation of the T cells by the CAR and the targeting of healthy cells that express the antigen, which is termed on-target, off-tumour toxicity. In addition, persistent activation of these alpha beta T cells due to antigen dependent or independent CAR activation, can lead to exhaustion and reduced bioactivity.

SUMMARY OF THE INVENTION

There is need for alternative CAR-based approaches with greater selectivity and reduced on target, off tumour toxicity.

The use of innate cells such as gamma delta T cells and NK cells as carriers of CAR has been reported. However, these studies employ CARs with similar signalling domains as the alpha beta T CAR, e.g. the CD3ζ and CD28 or CD137, which results in similar problems, such as on-target, off-tumour cytotoxicity.

The effector functions of gamma delta T and NK cells, unlike alpha beta T cells, are linked to molecules such as the FcγRs. The inventors have determined gamma delta T cells or NK cell expressing a CAR that includes stimulatory domains of Fcγ receptor common chain will result in increased effector functions (e.g. cytotoxicity, cytokine production, antigen acquisition and presentation) that can be employed in the development of cell therapies. The inventors have therefore developed CAR constructs which on binding of antigen to the extracellular portion of the CAR stimulate intracellular signalling domains, derived from Fcγ receptors, which causes activation of signalling pathways typically associated with Fcγ receptors.

It is considered a gamma delta T cell or NK cell or a cell expressing a T cell receptor associated with a gamma delta T cell or NK cell which further expresses a construct encoding a chimeric antigen receptor (CAR) that incorporates the signalling domain of one or more Fcγ receptors, including but not limited to signalling domains of Fc receptor γ chain, CD32a, CD32c or CD64, or functional variants and fragments thereof and combinations thereof may be capable of recognising a target cell and cause cell death in a manner similar to antibody-dependent cell-mediated cytotoxicity (ADCC) when bound to the target cell. The gamma delta T cells or NK cells expressing the construct may have increased effector functions such as increased inflammatory cytokine production, antigen acquisition and presentation or ability to activate adaptive immune responses. Suitably there is provided a gamma delta T cell or NK cell or a cell expressing a T cell receptor associated with a gamma delta T cell or NK cell which further expresses a construct encoding a chimeric antigen receptor (CAR) that consists or essentially consists of the signalling domain of one or more Fcγ receptors, including but not limited to signalling domains of Fc receptor γ chain, CD32a, CD32c or CD64, or functional variants and fragments thereof and combinations thereof may be capable of recognising a target cell and cause cell death in a manner similar to antibody-dependent cell-mediated cytotoxicity (ADCC) when bound to the target cell.

Accordingly, a first aspect of the present invention provides a cell selected from a gamma delta T cell, a NK cell, or a cell expressing gamma delta T cell or NK natural cytotoxicity receptors, wherein the cell further comprises a CAR comprising an intracellular cell signalling domain selected from one or more of a FcγR γ chain or CD32a or CD32c or CD64 or a functional variant thereof.

Suitably the CAR may comprise:

(i) an antigen-binding domain coupled to a trans-membrane domain, (ii) an intracellular activation signalling domain (endodomain) wherein the intracellular activation signalling domain comprises one or more Fcγ intracellular signalling domains, preferably selected from the signalling domain of at least one of the CD16 Fc Receptor (FcγR γ chain) or CD32a or CD32c or CD64 or combinations of the signalling domains, such that binding of antigen to the antigen binding domain of the CAR causes signalling by the intracellular signalling domain of the CAR.

Suitably signalling by the CAR comprising the intracellular signalling domain selected from at least one of the CD16 Fc Receptor (FcγR γ chain) or CD32a or CD32c or CD64 or combinations of the signalling domains in the cell selected from a gamma delta T cell, a NK cell, or a cell expressing gamma delta T cell or NK natural cytotoxicity receptors can promote cell death, for example in a manner similar to ADCC, of a cell bound by the CAR.

In embodiments, the antigen-binding domain of the CAR can be coupled to the trans-membrane domain via a spacer.

The CD16 signalling domain is the FcR γ chain and it is shared by a number of Fc receptors. In addition, CD32a and c and their signalling domains are expressed by gamma delta T cells and NK cells. These receptors and their signalling domains expressed by NK cells and gamma delta T cells are important for the effector function of the gamma delta and NK cells and mediate, for example, ADCC, cytokine production and antigen acquisition and presentation. Suitably, a construct to provide a CAR may be utilised with NK cells. Suitably, in embodiments, the CARs may include only intracellular signalling domains selected from a FcγR common chain or CD32a or CD32c or CD64.

In embodiments, the endodomain of the CAR expressed in a cell selected from a gamma delta T cell, a NK cell, or a cell expressing gamma delta T cell or NK natural cytotoxicity receptors comprises an intracellular signalling domain comprising one or more of a FcR γ chain or CD32a or CD32c which may comprise an intracellular domain with a sequence SEQ ID NO: 1 or SEQ ID NO: 2 or SEQ ID NO: 3 or functional variants or fragments thereof or a combination of these.

```
FcR γ chain
                                        SEQ ID NO: 1
MIPAVVLLLL LLVEQAAALG EPQLCYILDA ILFLYGIVLT

LLYCRLKIQV RKAAITSYEK SDGVYTGLST RNQETYETLK HEKPPQ

CD32a (FCGR2A)
                                        SEQ ID NO: 2
MTMETQMSQN VCPRNLWLLQ PLTVLLLLAS ADSQAAAPPK

AVLKLEPPWI NVLQEDSVTL TCQGARSPES DSIQWFHNGN

LIPTHTQPSY RFKANNNDSG EYTCQTGQTS LSDPVHLTVL

SEWLVLQTPH LEFQEGETIM LRCHSWKDKP LVKVTFFQNG

KSQKFSHLDP TFSIPQANHS HSGDYHCTGN IGYTLFSSKP

VTITVQVPSM GSSSPMGIIV AVVIATAVAA IVAAVVALIY

CRKKRISANS TDPVKAAQFE PPGRQMIAIR KRQLEETNND

YETADGGYMT LNPRAPTDDD KNIYLTLPPN DHVNSNN

CD32c (FCGR2C)
                                        SEQ ID NO: 3
MGILSFLPVL ATESDWADCK SPQPWGHMLL WTAVLFLAPV

AGTPAAPPKA VLKLEPQWIN VLQEDSVTLT CRGTHSPESD

SIQWFHNGNL IPTHTQPSYR FKANNNDSGE YTCQTGQTSL

SDPVHLTVLS EWLVLQTPHL EFQEGETIVL RCHSWKDKPL

VKVTFFQNGK SKKFSRSDPN FSIPQANHSH SGDYHCTGNI

GYTLYSSKPV TITVQAPSSS PMGIIVAVVT GIAVAAIVAA

VVALIYCRKK RISANSTDPV KAAQFEPPGR QMIAIRKRQP

EETNNDYETA DGGYMTLNPR APTDDDKNIY LTLPPNDHVN SNN
```

Whilst not wishing to be bound by theory, it is understood that antigen binding by a CAR, wherein the intracellular cell signalling domain of the CAR comprises one or more of a FcR γ chain or CD32a or c, expressed in a cell selected from a gamma delta T cell, a NK cell, or a cell expressing gamma delta TCR or NK natural cytotoxicity receptors, will lead to ITAM phosphorylation of the intracellular signalling domain by members of the Src-kinase family and subsequent recruitment of SH-2 containing kinases such as members of the Syk-kinase family. These will lead ultimately to the recruitment of phosphatidylinositol 3-kinase (PI3-K) and phospholipase-Cγ (PLCγ), which trigger protein kinase C (PKC) activation and sustained calcium elevation, leading to a functional outcome depending on the cell type expressing the CAR, but in the case of gamma delta T cells it will be ADCC, cytokine production (e.g. TNF) and potentially increased antigen acquisition and presentation.

In embodiments, a functional variant or fragment of the signalling domain of the expressed CAR may comprise one or more amino acid mutations of the "wild type" sequences provided as SEQ ID NO:1, SEQ ID NO:2 and SEQ ID NO:3, such as insertions/deletions/substitutions, suitably up to 20, 15, 10, 5 mutations selected from insertions/deletions/substitutions to insert/remove/replace one or more amino acids. Suitably at least one, two, three, four or five mutations may be provided wherein the endodomain of the CAR has one, two, three, four or five less or more or different amino acids than: the wild-type signal sequence from which it is derived.

In embodiments, the cell in which the CAR is expressed can be selected from a gamma delta T cell or a natural killer (NK) cell, suitably a gamma delta T cell.

In a second aspect of the invention there is provided a method for making a cell according to the first aspect of the invention, which comprises the step of introducing: a nucleic acid construct or vector which encodes a CAR comprising:
  (i) an antigen-binding domain coupled to a trans-membrane domain,
  (ii) an intracellular activation signalling domain (endodomain)
  wherein the intracellular activation signalling domain comprises one or more FcγR common intracellular signalling domains, preferably selected from the signalling domain of at least one of the CD16Fc Receptor (FcR γ chain) or CD32a or CD32c or CD64, or functional variants thereof or combinations of the signalling domains, such that binding of antigen to the antigen binding domain of the CAR causes signalling by the intracellular signalling domain of the CAR in a cell selected from a gamma delta T cell, a NK cell, a cell expressing gamma delta TCR or NK natural cytotoxicity receptors wherein the intracellular cell signalling domain comprises one or more FcR γ chain or CD32a or c or CD64.

In embodiments, a cell into which the construct or vector is introduced may be part of or derived from a sample isolated from a subject.

The cell used in the method of the second aspect of the invention may be from a sample isolated from a patient, a related or unrelated haematopoietic transplant donor, a completely unconnected donor, from cord blood, differentiated from an embryonic cell line, differentiated from an inducible progenitor cell line, or derived from a transformed cell line.

In a third aspect, the present invention provides a pharmaceutical composition comprising a plurality of cells according to the first aspect of the invention or provided by the method of the second aspect of the invention. The composition may be an autologous gamma delta T and/or NK cell composition.

In a fourth aspect, the present invention provides a method for treating and/or preventing a disease, which comprises the step of administering a plurality of cells according to the first aspect of the invention or provided by the method of the second aspect of the invention or a pharmaceutical composition according to the third aspect of the invention to a subject in need thereof.

The method may comprise the following steps:
  (i) optionally, isolating a gamma delta T and/or NK cell-containing sample from a subject;
  (ii) transducing or transfecting of gamma delta T and/or NK cell with a nucleic acid construct or vector encoding a CAR comprising
    (a) an antigen-binding domain coupled to a trans-membrane domain,
    (b) an intracellular activation signalling domain (endodomain)
  wherein the intracellular signalling domain comprises one or more Fcγ common chain intracellular signalling domains, preferably selected from the signalling domain of at least one of the FcR γ chain, CD16Fc Receptor or CD32a or CD32c or CD64 or a functional variant thereof or combinations of the signalling domains, such that binding of antigen to the antigen binding domain of the CAR causes signalling by the intracellular signalling domain of the CAR to produce an activated gamma delta T cell or a NK cell expressing the CAR; and
  (iii) administering the gamma delta T and/or NK cells from (ii) to a subject.

Suitably the subject to whom the gamma delta T cells or NK cells are administered may be the subject from whom the gamma delta T cells and/or NK cells were isolated. Alternatively, the subject to whom the gamma delta T cells or NK cells are administered may be a different subject from that whom the gamma delta T cells and/or NK cells were isolated. Suitably the subject to whom the gamma delta T cell or NK cell are administered may not be related to the subject from whom the cells were obtained.

There is also provided a cell of the first aspect of the invention, or a cell provided by the second aspect of the invention, or a pharmaceutical composition according to the third aspect of the invention for use in treating and/or preventing a disease.

There is also provided a cell of the first aspect of the invention, or a cell provided by the second aspect of the invention, in the manufacture of a medicament for treating and/or preventing a disease.

DETAILED DESCRIPTION

Chimeric Antigen Receptors (CARs)

CARs are chimeric type I trans-membrane proteins which connect an extracellular antigen-recognizing domain to an intracellular signalling domain (endodomain). The antigen recognising domain is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1 or IgG4. More compact spacers can suffice e.g. the stalk from CD8a and even just the IgG1 hinge alone, depending on the antigen. IgG domains can be modified to reduce binding to Fc receptors. A transmembrane domain anchors the protein in the cell membrane and connects the antigen binding site/spacer to the endodomain.

First generation CAR designs comprised endodomains derived from the intracellular parts of either the γ chain of the Fc εR1 or CD3ζ. These designs were mostly applied to alpha beta T cells. The activation signal initiated by these domains was sufficient to trigger T-cell killing of cognate target cells in in vitro assays but failed to fully activate the T-cell to proliferate and survive. It was soon discovered that the use of these domains resulted in alpha beta T cell anergy. Furthermore, it was also reported that the use of the γ chain of the Fc εR1 was not efficient in activating alpha beta T cells and thus was quickly abandoned. Second generation CAR designs comprised endodomains which included fusion of the intracellular part of a T-cell co-stimulatory molecule to that of CD3 ζ. These can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described, which include TNF receptor family endodomains, such as the closely related OX40 and 4-1BB, which transmit survival signals. The most commonly used costimulatory domains used in clinical trials are CD28 or 4-1BB (CD137).

Further CAR designs including a co-stimulatory signal portion, are as described for example by WO 2016/166544.

CAR-encoding nucleic acids may be transferred to T cells using, for example, retroviral vectors. Lentiviral vectors may be suitably employed.

In the present invention, in embodiments, the CARs, expressed in the gamma delta T cell, a NK cell, a cell expressing gamma delta TCR or NK natural cytotoxicity receptors wherein the intracellular cell signalling domain comprises one or more Fcγ receptor signalling domains, can be provided by:

(CD19scFv-linker-myc-CD28[EX]-FcR gamma[TM-IN])
SEQ ID NO: 4
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSAAASGGGGSEQKLISEEDLIEVMYPPPYLDNEK
SNGTIIHVKGKHLCPSPLFPGPSKPLCYILDAILFLYGIVLTLLYCRLKI
QVRKAAITSYEKSDGVYTGLSTRNQETYETLKHEKPPQAAA.

(CD19scFv-linker-myc-CD28[EX-TM]-FcR gamma[IN])
SEQ ID NO: 5
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSAAASGGGGSEQKLISEEDLIEVMYPPPYLDNEK
SNGTIIHVKGKHLCPSPLFPGPSKPFWVLVVVGGVLACYSLLVTVAFIIF
WVRLKIQVRKAAITSYEKSDGVYTGLSTRNQETYETLKHEKPPQ.

(CD19scFv-linker-myc-CD28[EX-TM]-CD32a[IN])
SEQ ID NO: 6
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSAAASGGGGSEQKLISEEDLIEVMYPPPYLDNEK
SNGTIIHVKGKHLCPSPLFPGPSKPFWVLVVVGGVLACYSLLVTVAFIIF
WVCRKKRISANSTDPVKAAQFEPPGRQMIAIRKRQLEETNNDYETADGGY
MTLNPRAPTDDDKNIYLTLPPNDHVNSNN.
or (CD19scFv-linker-myc-CD28[EX-TM]-CD32c[IN])
SEQ ID NO: 7
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSAAASGGGGSEQKLISEEDLIEVMYPPPYLDNEK
SNGTIIHVKGKHLCPSPLFPGPSKPFWVLVVVGGVLACYSLLVTVAFIIF
WVCRKKRISANSTDPVKAAQFEPPGRQMIAIRKRQPEETNNDYETADGGY
MTLNPRAPTDDDKNIYLTLPPNDHVNSNN.

EX = extracellular domain

TM = transmembrane domain

IN = intracellular domain

Suitably a functional variant of the sequence shown as SEQ ID NOs: 4, 5, 6 or 7 may be provided for example, with at least 80, 85, 90, 95, 98 or 99% sequence identity, provided that the functional variant is a CAR able to bind the antigen described and provide a signal via the intracellular signalling domain capable of activating the T cell or NK cell when in combination with the gamma delta T cell receptor or NK receptor signalling. Suitably embodiments of a CAR construct of the present invention may be provided by any one of SEQ ID NOs: 4, 5, 6 or 7. Methods of sequence alignment and determination of sequence identity are well known in the art and can be accomplished using suitable alignment programs. The % sequence identity refers to the percentage of amino acid or nucleotide residues that are identical in the two sequences when they are optimally aligned. Nucleotide and protein sequence homology or identity may be determined using standard algorithms, such as a BLAST program (Basic Local Alignment Search Tool at the National Center for Biotechnology Information) using default parameters, which is publicly available at http://blast.ncbi.nlm.nih.gov. Other algorithms for determining sequence identity or homology include: LALIGN (http://www.ebi.ac.uk/Tools/osa/lalign/and http://www.ebi.ac.uk/Tools/psa/lalign/nucleotide.html). AMAS (Analysis of Multiply Aligned Sequences, at http://www.compbio.dundee.ac.uk/Software/

Amas/amas.html). FASTA fhttp://www.ebi.ac.uk/Tools/sss/fasta/), Clustal Omega (http://www.ebi.ac.uk/Tools/msa/clustalo/). SIM (http://web.expasv.org/sim/). and EMBOSS Needle (http://www.ebi.ac.uk/Tools/psa/emboss needle/nucleotide.html).

Binding of the CAR expressed by the cells to the desired antigen can be tested by using a chimeric protein, comprising the antigen targeted by the CAR and the Fc portion of human IgG. Binding of the chimeric protein to the CAR can be detected by methods such as flow cytometry, western blot, enzyme-linked immunosorbent assay (ELISA) using appropriate secondary antibodies detecting the Fc portion of the chimeric protein.

In other aspects of the invention the functionality of the CAR expressing γδ T or NK cells can be tested against cancer cell lines or primary tumour cell expressing the targeted antigen by methods know to the art including, but not limited to, Annexin V/PI cytotoxicity assays, chromium release assay, CD107 degranulation assays, intracellular cytokine assays, Luminex. Appropriate controls such as non-transduced γδ T or NK cells and cell lines that do not express the targeted antigen can be employed to demonstrate that the increased effector functions are due to specific CAR activity.

In embodiments of the invention a CAR comprising signalling domains of CD32a or CD32c is expressed by a γδ T cell. Engagement of the CAR to its target initiates signalling that can result in increased antigen acquisition and presentation by the γδ T cell expressing the CAR. γδ T cells can acquire and present antigen to initiate and propagate adaptive immune responses (Brandes et al, Science, 2005). γδ T cell can acquire antigen by interaction with opsonised target cells (Himoudi et al, JI 2012) and act as professional antigen presenting cells. Without wishing to be bound by theory, it is considered that a γδ T cell expressing a CAR comprising CD32a or CD32c or FcR γ chain costimulatory domains will have enhanced antigen acquisition and presentation capability. In embodiments, the increased abilities of the CAR expressing cells of the invention to acquire and present antigen can be demonstrated by assays known to the art including, but not limited to, phagocytosis of fluorescent beads expressing the target antigen or by detecting antigen presentation using model antigens and antibodies that recognise HLA-peptide antigens.

Antigen Binding Domain

The antigen binding domain is the portion of the CAR which recognizes antigen. Antigen-binding domains can include the antigen binding site of an antibody an antibody fragment, single-chain variable fragment (scFv), a single domain antibody (sdAb), a Fab, F(ab)2, an Fc, the light and heavy chains of an antibody, or any combinations thereof that bind to a cell surface disease related antigen, or a peptide derived from a diseased associated antigen expressed as a complex with Major Histocompatibility Complex (MHC). In embodiments, the antigen binding moiety can be a bispecific construct, comprising two different antibodies directed to two different antigens, different epitopes of the same antigen, or a disease associated antigen and a costimulatory or co-inhibitory molecule(s) or a homing/migration receptor(s). In other embodiments of the invention the antigen binding domain can be an alpha beta T cell receptor or a gamma delta T cell receptor. Antibodies for use in antigen binding domain can be derived from human B-cells, mouse B cells, a rat B cell, or from hybridoma cell lines. A hybridoma cell line can be derived from immunized wild type or humanized mice, a rat B-cell, a rat hybridoma cell isolated from immunized wild type or humanized rats, or from antibody libraries derived from human, mouse, rat, camel, shark or llama. For example, the antigen-binding domain may comprise: a single-chain variable fragment (scFv) derived from a monoclonal antibody; a natural ligand of the target antigen; a peptide with sufficient affinity for the target; a single domain antibody; or a single-chain derived from a T-cell receptor.

Suitably, the extracellular antigen binding domain may recognise and bind to a tumour-specific or disease-associated antigen which is present only on tumour/diseased cells and not on any other cells and/or a disease-associated antigen which is present on some diseased cells and also some normal cells. Such disease associated antigens may include, but are not limited to, CD19, EGFR, EGFRvRIII, ErbB2, GM3, GD2, GD3, CD20, CD22, CD30, CD37, CD38, CD70, CD75, CD79b, CD33, CD138, gp100, NY-ESO-1, MICA, MICB, MART1, AFP, ROR1, ROR2, PSMA, PSCA, mutated Ras, p53, B-Raf, c-met, VEGF, carbonic anhydrase IX, WT1, carcinoembryonic antigen, CA-125, MUC-1, MUC-3, epithelial tumour antigen and a MAGE-type antigen including MAGEA1, MAGEA3, MAGEA4, MAGEA12, MAGEC2, BAGE, GAGE, XAGE1B, CTAG2, CTAG1, SSX2, or LAGE1 or viral antigens or combinations thereof or post-translationally modified proteins that may include, but are not limited to, carbamylated and citrunillated proteins.

In embodiments, an antigen binding domain can bind an antigen found in a cell infection, bacterial infection, fungal infection, protozoan infection or virus infection or an active or inactivated viral fragment, a peptide, a protein, an antigenic segment or the like from a virus.

In embodiments, the extracellular antigen binding domain may recognise an immune checkpoint ligand, for example PD-L1.

In embodiments, the antigen binding domain may be the extracellular portion of a cell surface receptor which is then fused to the transmembrane and co-stimulatory domains as described above.

Spacer Domain

CARs typically comprise a spacer sequence to connect the antigen-binding domain with the transmembrane domain. The spacer domain separates the antigen-binding domain from the endodomain and a flexible spacer can allow the antigen-binding domain to orient in different directions to facilitate binding.

The spacer sequence for a CAR may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

(hinge-CH2CH3 of human IgG1)
SEQ ID NO: 8
AEPKSPDKTHTCPPCPAPPVAGPSVFLFPPKPKDTLMIARTPEVTCVVVDV

SHEDPEVKFNWYVDGVEVHNAKTKPREEQYNSTYRWSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGKKD

-continued (human CD8 stalk):
SEQ ID NO: 9
TTTPAPRPPTPAPTIASQPLSLRPEACRPAAGGAVHTRGLDFACDI (human IgG1 hinge):
SEQ ID NO: 10
AEPKSPDKTHTCPPCPKDPK (CD2 ectodomain)
SEQ ID NO: 11
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCP EKGLD (CD34 ectodomain)
SEQ ID NO: 12
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT (human CD28 stalk)
SEQ ID NO: 13
IEVMYPPPYLDNEKSNGTIIHVKGKHLCPSPLFPGPSKP (SGGGS linker)
SEQ ID NO: 14
SGGGGS (myc tag)
SEQ ID NO: 15
EQKLISEEDL

TRANSMEMBRANE DOMAIN

The transmembrane domain is the sequence of the CAR that spans the membrane.

A transmembrane domain may be any protein structure which is thermodynamically stable in a membrane.

The transmembrane domain may be derived from CD28, which gives good receptor stability. Alternatively, the transmembrane region may be derived from CD3, CD4, CD8, FcγR γ chain, CD16 (Fcγ RIIIA), CD32a (Fcγ RIIA), CD32c (Fcγ RIIC) or CD64 (Fcγ RIA).

Signalling Domain

The activating endodomain of the CAR may comprise, consist essentially, or consist of a signalling domain of Fcγ receptors. Examples of these receptors are Fcγ RIIIA (CD16), Fcγ RIIA (CD32a), Fc γ RIIC (CD32c), or Fcγ RIA (CD64). In embodiments, the CAR can include activating domains from the FcR γ chain, Fcγ RIIA (CD32a), Fcγ RIIC (CD32c) or combination of these. In embodiments of the invention the activation endodomains of the Fcγ receptors can be combined with other activation domains including but not limited to CD28, CD2, ICOS, JAMAL, CD27, CD30, OX40, CD46, CD137 (4-1BB), Dynax Activating Protein (DAP)-10, DAP-12, IL-2 common γ chain, IL-12 receptor, CD244.

Suitably the intracellular signalling sequence can comprise the "wild type" intracellular signalling domain of the FcR γ chain (SEQ ID NO:1), CD32a (SEQ ID NO:2) or CD32c (SEQ ID NO:3).

Suitably, variants of the proposed "wild type" intracellular signalling sequences can be provided wherein a variant sequence of the Fcγ receptor activating domain may have at least 80%, 85%, 90%, 95%, 98% or 99% sequence identity to SEQ ID NO:1 or SEQ ID NO:2 or SEQ ID NO:3, provided that the sequence provides an effective intracellular cell signalling domain.

Suitably, the activity of the signalling domain of the CAR may be tested by methods know in the art. These can include intracellular flow cytometry staining against phosphorylated forms of signalling molecules downstream of the signalling cascade initiated by the domains incorporated in the CAR, such as SYK, ERK, p38 and JNK, or measurement of intracellular calcium changes. Selective engagement of the CAR using recombinant or chimeric proteins may be used to initiate CAR engagement to stimulate signalling. Suitably, the activity of the signalling domains may be assessed using functional assays that determine downstream effector functions initiated by CAR engagement. This may include but is not limited to Annexin V/PI cytotoxicity assays, chromium release assay, CD107 degranulation assays, intracellular cytokine assays, or Luminex. Appropriate controls such as non-transduced γδ T or NK cells and cell lines that do not express the targeted antigen may be employed to demonstrate that the increased effector functions are due to specific CAR activity.

In embodiments of the invention, the nucleic acid sequence encoding a CAR may include a leader sequence which will direct the protein to the cell membrane (such as the GMCSF-R secretory signal or CD8).

Cell

A cell comprising a CAR of the first aspect may be an immune effector cell such as a gamma delta (gamma delta) T cell or a natural killer (NK) cell.

Gamma delta T cells are immune cells with innate-like properties that are indispensable for effective immunity against infections and cancer. Unlike alpha beta (alpha beta) T cells they express the gamma and delta chain of the TCR and it is believed they have a more limited clonal diversity. Gamma delta T cells recognise non-peptide antigens in a non-MHC restricted manner. In the blood, they represent a minor subset in humans (less than 10%). Their majority of gamma delta T cells express Vγ9Vδ2 (gamma 9 delta 2) T cell receptor, which recognises the endogenous isopentenyl pyrophosphate (IPP) that is over produced specifically in cancer cells as a result of a dysregulated mevalonate pathway. This allows the gamma delta T cells to distinguish healthy from transformed cells. In addition, gamma delta T cells express a number of NK cell receptors, such as CD56, NKG2D, NKp80 and NKp46 that mediate their cytotoxic functions. The ability of gamma delta T lymphocytes to produce abundant pro inflammatory cytokines like IFN-gamma and TNF, their potent cytotoxic effective function and MHC-independent recognition of antigens makes them an important tool for cancer immunotherapy. Gamma delta T cells have been indicated to be able to kill many different types of tumour cell lines in vitro, including leukaemia, neuroblastoma, and various carcinomas. Further, it has been demonstrated that gamma delta T cells can recognise and kill many different differentiated tumour cells either spontaneously or after treatment with different bisphosphonates, including zoledronate. Bisphosphonate treatment results in accumulation of endogenous IPP that promotes activation of gamma delta T cells.

NK cells are part of the innate immune system endowed with potent cytolytic function that provide host defence against microbial infections and tumours. They are characterised phenotypically as $CD3^-CD56^+$ lymphocytes in humans and express a number of natural cytotoxicity receptors (NCR) that regulate their functions. Upon activation, NK cells demonstrate direct cytotoxicity and express pro-inflammatory cytokines such as IFN gamma and TNF.

Unlike alpha beta T cells, gamma delta T cells and NK cells mediate their function through Fcγ receptors and mediate ADCC through them. Both cell types express Fcγ receptors and ADCC is understood to be mediated primarily by the Fcγ RIIIA (CD16) receptor. In addition, it is understood that gamma delta T cells acquire antigen after physical interaction with antibody coated target cells. This interaction is facilitated by Fcγ receptors expressed on gamma delta T cells, suitably Fcγ RIIIA (CD16), Fcγ RIIA (CD32a) and Fcγ RIIC (CD32c). Expression of CAR that include activation domains from Fcγ receptors are considered by the inventors to mimic the natural engagement of these receptors by antibodies and to generate a biological effect in innate immune cells such as gamma delta T cells or NK cells. Alpha beta T cells would not be suitable hosts for a CAR construct including a Fcγ common intracellular signalling domain as the alpha beta T cells do not mediate their functionality through Fcγ receptors. Gamma delta T cells expressing the described CAR will have increased cytotoxic potential, effector cytokine production and ability to acquire and present disease associated antigens. The latter effect can increase their ability to induce adaptive alpha beta immune responses.

CAR-expressing cells may either be created ex vivo either from a patient's own peripheral blood (1st party), or via a haematopoietic stem cell transplant from donor peripheral blood (2nd party), or peripheral blood from an unconnected donor (3rd party).

The present invention also provides a cell composition comprising CAR-expressing cells, such as CAR-expressing gamma delta T and/or NK cells, according to the present invention. The cell composition may be made by transducing a blood-sample ex vivo with a nucleic acid construct according to the present invention.

Alternatively, CAR-expressing cells may be derived from ex vivo differentiation of inducible progenitor cells or embryonic progenitor cells to the relevant cell type, such as gamma delta T cells. Alternatively, an immortalized cell line such as a gamma delta T-cell line which retains its lytic function and could act as a therapeutic may be used.

In all these embodiments, CAR cells may be generated by introducing DNA or RNA coding for the CAR by one of many means including transduction with a viral vector, or transfection with DNA or RNA.

A CAR T cell of the invention may be an ex vivo gamma delta T cell from a subject. Suitably, gamma delta T cells for use in the invention may be generated from blood mononuclear cells (BMCs) or biopsies from cancer or infected tissues. Suitably, BMCs may be obtained via any density centrifugation method known to those skilled in the art from either whole blood, leukapheresis material or umbilical cord blood (UCB). Density centrifugation methods may include, but are not limited to, ficoll gradient or lymphoprep. In addition, cell isolation can be performed by magnetic-activated cell sorting (MACS) or fluorescence-activated cell sorting (FACS).

Suitably, in embodiments gamma delta T cells may be expanded from peripheral blood mononuclear cells (PBMCs), cord blood mononuclear cells (CBMCs) or tissue derived cells in a chemically defined culture medium which can include, but is not limited to, ALyss505, RPMI, Tex-MACS, IMDM, CTS OpTmizer, X-VIVO 10 or AIM-V media. Cell culture medium can be supplemented with either foetal calf serum (FCS), human AB serum, autologous plasma, human platelet lysate or chemically defined serum replacement substitutes for example CTS Immune Serum Replacement. Further, serum/plasma/serum substitute is added in an amount of 0.1 to 20% (v/v) to the culture solution.

Suitably, in embodiments gamma delta T cells of the Vgamma9 subtype may be selectively expanded from PBMCs or CBMCs or tissue derived cells in a chemically defined culture medium, including IL-2, serum/plasma/serum substitute and activation by the provision of an aminobisphosphonate such as zoledronic acid. Multiple gamma delta TCR isotypes may be used from any gamma delta TCR pairing from Vγ1-9 and Vδ1-8. It will be understood by those of skill in the art that culture conditions, specifically the method of TCR activation, will define the isotype to be expanded. By way of example, δ2 T cells are activated and expanded by aminobisphosphonates and the like, whilst δ1 T cells may be preferentially expanded using NKG2D ligands such as MICA or MICB or anti-TCR antibodies. Isolated PBMCs/CBMCs may be freshly isolated or cryopreserved prior to expansion in culture.

A bisphosphonate is an analogue of pyrophosphoric acid and is a compound in which the O (oxygen atom) of the pyrophosphoric acid skeleton P—O—P is substituted with C (carbon atom) (P—C—P). It is generally used as a therapeutic drug for osteoporosis. The aminobisphosphonate refers to a compound having N (nitrogen atom) among the bisphosphonates. For example, the aminobisphosphonate used in the present invention is not particularly limited; examples thereof include pamidronic acid, its salt and/or their hydrate, alendronic acid, its salt and/or their hydrate, and zoledronic acid, its salt and/or their hydrate. The concentration of the aminobisphosphonates is preferably 1 to 30 μM for pamidronic acid, its salt and/or their hydrate, 1 to 30 μM for alendronic acid, its salt and/or their hydrate, and 0.1 to 10 μM for zoledronic acid, its salt and/or their hydrate. Here, 5 μM zoledronic acid is added as an example.

Suitably, antigen provision via aminobisphosphonate may be substituted with synthetic antigens such as isopentenyl pyrophosphate (IPP), phosphostim/bromohydrin pyrophosphate (BrHPP), (E)-4-Hydroxy-3-methyl-but-2-enyl pyrophosphate (HMBPP) or DMAPP. Antigenic stimulation may also be provided by co-culturing with irradiated and/or artificial antigen presenting cells (aAPC). The addition of such components provides a culturing environment which allows for positive selection of gamma delta T cells typically at 70%-100% by number of total cells in the culture sample.

The expansion of gamma delta T cells may be also stimulated with one or more antibodies against CD3, gamma delta TCR, CD28 and CD137. These can be soluble, plate bound or conjugated to appropriate beads, such as dynabeads or MACSibeads.

Gamma delta T cells may be propagated and expanded using any of the methodologies previously disclosed. Gamma delta T cells of any isotype may be selectively expanded for a time-frame of at least 7 days, more preferably 14 days. Suitably, the period of culturing may be performed for about 9 days or greater to achieve high numbers of substantially purified CAR-expressing gamma delta T cell populations. Gamma delta T cells may be expanded using TCR antigens or NKG2D ligands such as MICA or MICB. Expanded gamma delta T cells may be cryopreserved and resuscitated at a later time point for further expansion in culture.

Suitably, the cytokine IL-2 may also be included at 501 U/ml to 20001 U/mL, more preferably 4001 U/mL to 10001 U/mL. Suitably, the culture may also be supplemented with one or more cytokines such as IL-15, IL-18, IL-7, IL-4, IL-9 or IL-21 at 501 U/ml to 20001 U/ml.

The cells can be cultured in a suitable culture apparatus included but not limited to tissue culture flask, G-REX, bags or automated cell culture system such as the Miltenyi Prodigy.

A CAR-expressing cell of the invention maybe an NK-cell. Suitably the NK cell of the invention may be generated from blood mononuclear cells (BMCs) or biopsies from cancer or infected tissues. Suitably, BMCs may be obtained via any density centrifugation method known to those skilled in the art from either whole blood, leukapheresis material or umbilical cord blood (UCB). Density centrifugation methods may include, but are not limited to, ficoll gradient or lymphoprep. In addition, cell isolation can be performed by magnetic-activated cell sorting (MACS) or fluorescence-activated cell sorting (FACS).

Suitably in aspects of the invention the starting material for the expansion of the NK cells may be depleted of cells expressing CD3 using methods known to the skilled in the art such as MACS.

NK cells may be expanded from PBMCs, CBMCs, tissue derived cells or from material that is depleted from CD3+ cells in a chemically defined culture medium, which can include but is not limited to, ALyss505, RPMI, TexMACS, IMDM, CTS OpTmizer, X-VIVO 10 or AIM-V media. Cell culture medium can be supplemented with either foetal calf serum (FCS), human AB serum, autologous plasma, human platelet lysate or chemically defined serum replacement substitutes for example CTS Immune Serum Replacement. Further, serum/plasma/serum substitute is added in an amount of 0.1 to 20% (v/v) to the culture solution.

For the expansion of NK cells, the cytokine IL-2 may also be included at 501 U/ml to 20001 U/ml, more preferably 4001 U/mL to 1000 IU/ml. Suitably, the culture may also be supplemented with one or more cytokines such as IL-15, IL-18 or IL-21 at 501 U/ml to 2000 IU/ml.

Suitably, CAR-expressing cells can be selectively expanded with the use of a recombinant protein recognised by the CAR e.g. recombinant CD19-Fc chimera or recombinant CD19 in the case of a CD19-targeted CAR. This can be plate bound, soluble or on appropriate beads, such as dynabeads or MACSibeads. Alternatively, aAPCs expressing the antigen recognised by the CAR can be employed for selective expansion of the CAR-expressing cells, such as K562 cells genetically modified to express CD19, in the case of a CD19 targeting CAR.

The method of genetically modifying a gamma delta T cell or NK cells to incorporate the nucleic acid encoding a CAR of the present invention may include any technique known to those skilled in the art.

Suitable methodologies include, but are not restricted to, viral transduction with viruses e.g. lentiviruses/retroviruses/adenoviruses, cellular transfection of nucleic acids by electroporation, nucleofection, lipid-based transfection reagents, nanoparticles, calcium chloride based transfection methods or bacterially-derived transposons, DNA transposons or retrotransposons, TALENS or CRISPR/Cas9 technologies.

Suitably, the nucleic acid may take the form of DNA (cDNA, plasmid, linear, episomal, minicircle), RNA or in vitro transcribed (IVT) RNA. In addition to the nucleic acid encoding the CAR sequences, the nucleic acid may also encode for proteins/enzymes/sequences required to aid integration of the genetic information into the host genome.

When lentiviruses/retroviruses/adenoviruses are employed for transduction, inclusion of chemical reagents as would be understood by those skilled in the art to enhance this process can be used. These include for example, but are not limited to, hexadimethrine bromide (polybrene), fibronectin, recombinant humanfibronectin (such as RetroNectin-Takara Clontech), DEAE dextran and TransPlus Virus Transduction Enhancer (ALSTEM Cell Advancements), Lentiboost (Sirion Biotech), Protamine Sulphate.

Suitably, incorporation of nucleic acids encoding a CAR may be introduced to gamma delta T or NK cells, peripheral blood mononuclear cells (PBMCs), cord blood mononuclear cells (CBMCs) or tissue derived expanded gamma delta T or NK cells at any time-point over the culturing period.

A CAR-expressing cell of the invention may be made by:
(i) isolating a gamma delta T cell or NK-cell-containing sample from a subject or other sources listed above; and
(ii) transducing or transfecting the gamma delta T cells on NK cells with a nucleic acid construct encoding the CAR including an intracellular signalling domain selected from Fcγ RIIIA (CD16), Fcγ RIIA (CD32a), Fcγ RIIC (CD32c), and CD64. The T cells or NK cells may then by purified, for example, selected on the basis of expression of the CAR.

Vector

A vector which comprises a CAR-encoding nucleic acid construct as defined herein may be used to introduce the nucleic acid sequence(s) into a host cell so that it expresses the CAR.

The vector may, for example, be a plasmid or a viral vector, such as a retroviral vector or a lentiviral vector, or a transposon based vector or synthetic mRNA.

The vector backbone may contain a bacterial origin of replication such as, for example, pBR322 and a selectable marker conferring resistance to an antibiotic, such as, but not limited to, the beta-lactamase gene conferring resistance to the antibiotic ampicillin to allow for sufficient propagation of the plasmid DNA in a bacterial host. Optionally, the vector may include the bacterial and phage attachment sites (attB and attP) of an integrase such as phiC31 in combination with the recognition sites of an endonuclease such as I-Scel to allow the production of minicircles devoid of the bacterial backbone. The vector will also include a sequence which encodes for expression of the CAR linked to a suitable promoter sequence for expression in the target cell of interest, most preferably a gamma delta T cell or NK cell. Optionally, the vector may include an antibiotic resistance gene, for positive selection in mammalian cells and may also include a reporter gene for identification of expression such as, but not limited to, green fluorescence protein (GFP). Additional reporter and/or selection gene expression may be driven from individual promoters, a bi-directional promoter or achieved by use of an IRES or self-cleaving T2A sequence.

The vector may be capable of transfecting or transducing a gamma delta T cell or NK cell.

Pharmaceutical Composition

The present invention also relates to a pharmaceutical composition containing a plurality of CAR-expressing cells, such as gamma delta T cells or NK cells, of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The cells of the present invention may be capable of killing target cells, such as cancer cells. The cells of the present invention may be used for the treatment of an infection, such as a viral infection.

The cells of the invention may also be used for the control of pathogenic immune responses, for example in autoimmune diseases, allergies and graft-vs-host rejection. The cells of the invention may be used for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

It is particularly suited for treatment of solid tumours where the availability of good selective single targets is limited.

The cells of the invention may be used to treat: cancers of the oral cavity and pharynx which includes cancer of the tongue, mouth and pharynx; cancers of the digestive system which includes oesophageal, gastric and colorectal cancers; cancers of the liver and biliary tree which includes hepatocellular carcinomas and cholangiocarcinomas; cancers of the respiratory system which includes bronchogenic cancers and cancers of the larynx; cancers of bone and joints which includes osteosarcoma; cancers of the skin which includes melanoma; breast cancer; cancers of the genital tract which include uterine, ovarian and cervical cancer in women, prostate and testicular cancer in men; cancers of the renal tract which include renal cell carcinoma and transitional cell carcinomas of the utterers or bladder; brain cancers including gliomas, glioblastoma multiforme and medullobastomas; cancers of the endocrine system including thyroid cancer, adrenal carcinoma and cancers associated with multiple endocrine neoplasm syndromes; lymphomas including Hodgkin's lymphoma and non-Hodgkin lymphoma; Multiple Myeloma and plasmacytomas; leukaemias both acute and chronic, myeloid or lymphoid; and cancers of other and unspecified sites including neuroblastoma.

According to a further aspect of the present invention there is provided a composition comprising a cell of the present invention together with a therapeutic agent.

Suitably, the therapeutic agent may be selected from the group consisting of a radionucleotide, boron, gadolinium or uranium atoms, an immunomodulator, an immunoconjugate, a cytokine, a hormone, a hormone agonist, an enzyme, an enzyme inhibitor, a photoactive therapeutic agent, a cytotoxic drug, a toxin, an angiogenesis inhibitor, immune-checkpoint inhibitor, a therapeutic antibody, antibody-drug conjugate (ADC) or a combination thereof.

The therapeutic agent may comprise an immunoconjugate/ADC comprising a cytotoxic drug. Suitably the cytotoxic drug may be a drug, a prodrug, an enzyme or a toxin.

In embodiments, the method of treating a cancer in a subject, suitably a mammal, particularly a human, can comprise treating the subject with a therapeutically effective amount of a cell of the present invention. In embodiments, the cell may be provided in a therapeutically effective formulation of cells in a dosage of $1 \times 10^4$ cells per kg of body weight, to over $5 \times 10^8$ cells per kg of body weight of the subject per dose.

In embodiments, the method can comprise repeatedly administering a therapeutically effective formulation of cells.

Suitably, tumour response can be assessed for changes in tumour morphology, for example in relation to tumour burden, tumour size and the like or using MRI scanning, x-ray scanning, CT scanning, bone imaging or biopsy sampling. Herein, an isolated nucleic acid molecule may be a nucleic acid molecule that is identified and separated from at least one contaminate nucleic acid molecule with which it is ordinarily associated with the natural source of the nucleic acid.

In embodiments, the cells of the current invention will be used to treat a viral infection, wherein said virus is HIV, influenza, hepatitis B, hepatitis C, influenza, Herpes variants, Cytomegalovirus (CMV), Epstein Barr Virus, Chickenpox, Papillomavirus, Varicella Zoster virus or Smallpox.

In embodiments, the influenza virus can be influenza A (Flu A) virus. In embodiments, the influenza virus can be an avian or swine—origin pandemic influenza virus, for example, H5N1, H7N3, H7N7, H7N9 and H9N2 (avian subtypes) or H1N1, H1N2, H2N1, H3N1, H3N2 H2N3 (swine subtypes).

In embodiments, there is provided gamma delta T cells for the treatment of a subject with cancer or infection wherein said treatment is allogeneic.

Treatment with the cells of the invention may help prevent the escape or release of tumour cells which often occurs with standard approaches.

According to a further aspect of the present invention constructs of CARs comprising at least one intracellular signalling domain selected from Fcγ RIIIA (CD16), Fcγ RIIA (CD32a), Fcγ RIIC (CD32c), and CD64 or combinations thereof are provided.

The invention will now be further described by way of Examples and the Figures, which are meant to serve to assist one of ordinary skill in the art in carrying out the invention and are not intended in any way to limit the scope of the invention.

FIGURES

Figure 1:
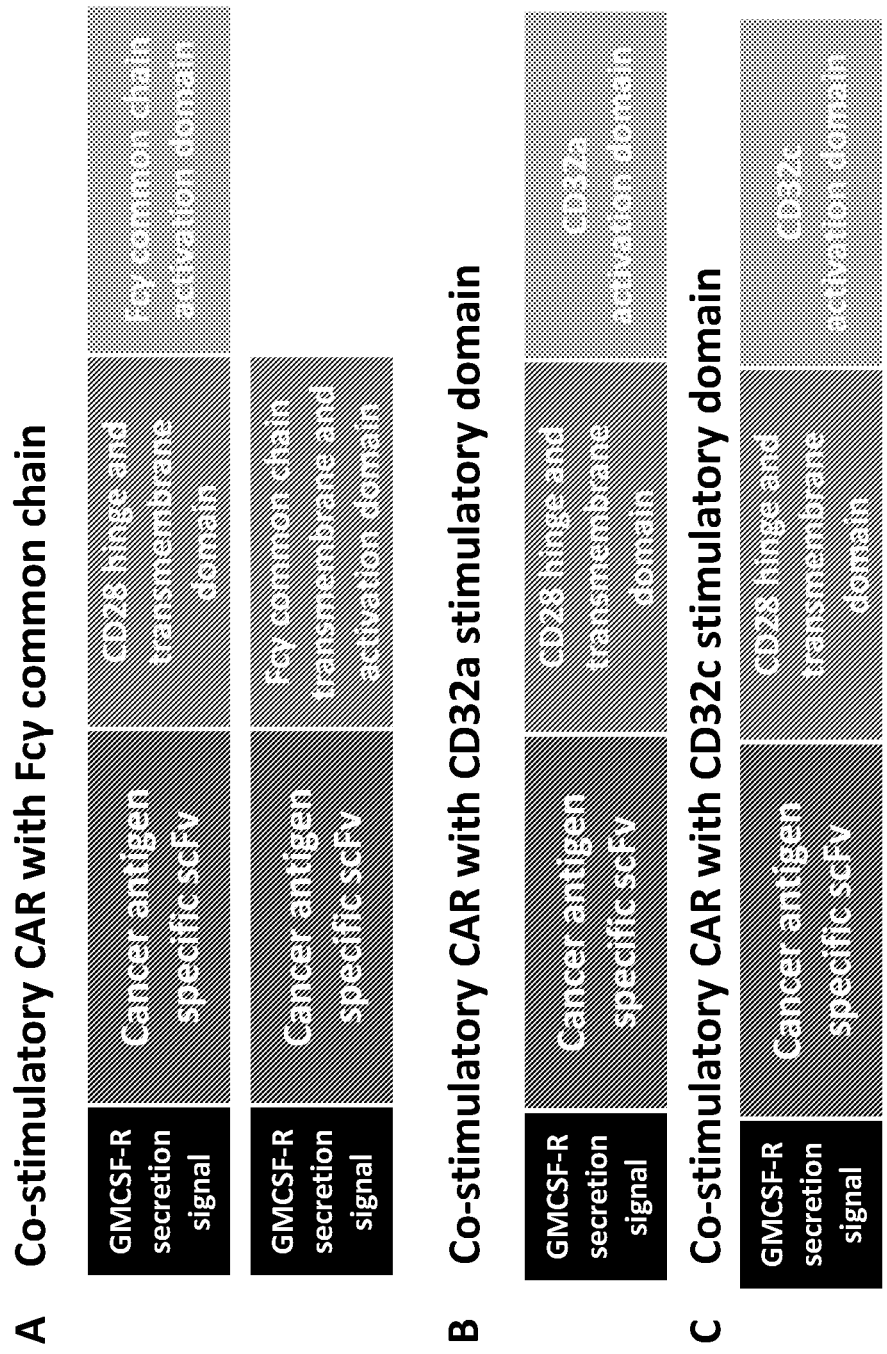

FIG. 1 illustrates proposed structures of the CAR constructs containing the activating domains of Fcγ receptors.

FIG. 2 illustrates a mechanism of action of gamma delta T cells expressing a CAR containing an activation domain from Fcγ receptors, wherein the gamma delta T cells expressing a Vgamma9 Vdelta2 TCR are activated by phosphoantigens specifically accumulated in cancer cells and concurrent CAR signalling after antigen engagement results in ITAM phosphorylation and eventually PKC pathway activation—resulting in increased cytotoxicity, cytokine production and potentially increased antigen presentation by the CAR-expressing gamma delta T cells.

FIG. 3 A) Gamma delta T cells were transduced to express a CAR comprising of an anti-CD19 scFv, a CD28 stock and transmembrane region and a Fcγ signalling endodomain. The gamma delta T cells were expanded and CAR expression was investigated by flow cytometry. B) CAR transduced and non-transduced cells were cocultured with the Burkitt's lymphoma cell line at a 10:1 ratio and their cytotoxic ability was assessed by flow cytometry based on Annexin V and PI staining. CAR-transduced gamma delta T cells exhibited almost twofold cytotoxic capacity compared with non-transduced (control) gamma delta T cells.

Figure 4:
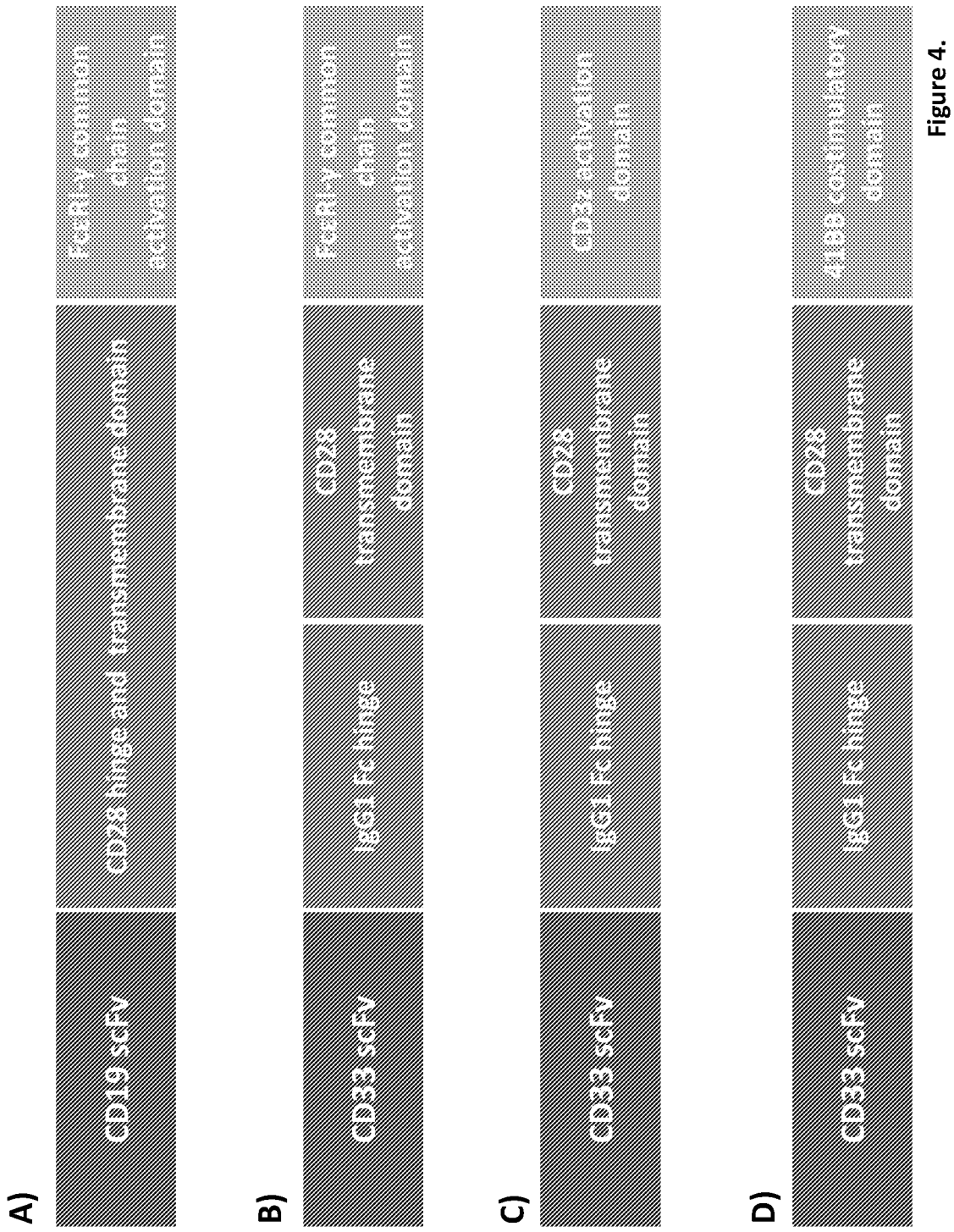

FIG. 4 illustrates schematic representations of CAR constructs. A) CD19 targeting CAR construct with a FcεRI-γ endodomain. B) CD33 targeting CAR construct with a Fcγ endodomain. C) CD33 targeting CAR construct with a CD3z endodomain. D) CD33 targeting CAR construct with a 41BB costimulatory endodomain.

Figure 5:
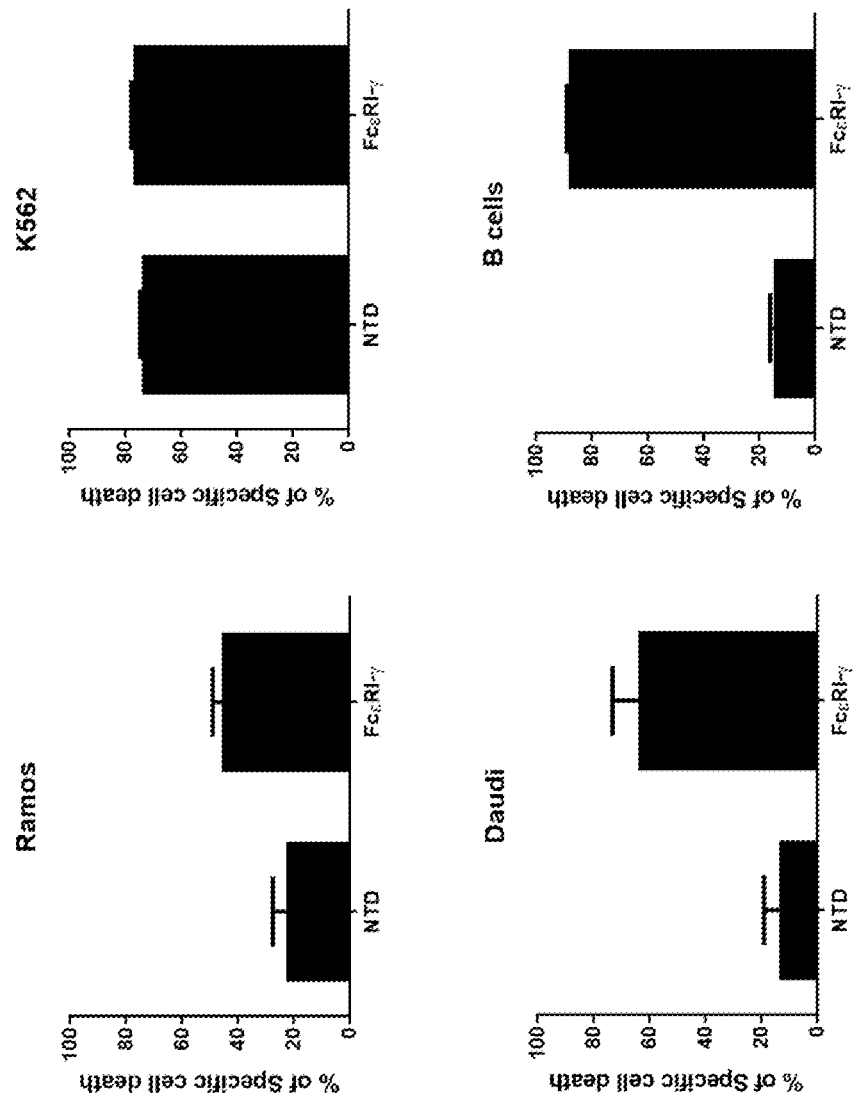

FIG. 5 illustrates Gamma delta T cells transduced to express a CAR comprising of an anti-CD19 scFv, a CD28 stalk and transmembrane region and a FcεRI-γ signalling endodomain as depicted in FIG. 4. The cells were co-incubated with CD19 positive Ramos and Daudi cancer cells, CD19 negative K562 cancer cells and CD19 positive healthy B cells at 10:1 ratio and their cytotoxic ability was assessed by flow cytometry based on Annexin V and PI staining. CAR-transduced gamma delta T cells exhibited significant additional cytotoxicity against CD19 positive cells but not against the CD19 negative K562 cells as compared to non-transduced (control) gamma delta T cells.

Figure 6:
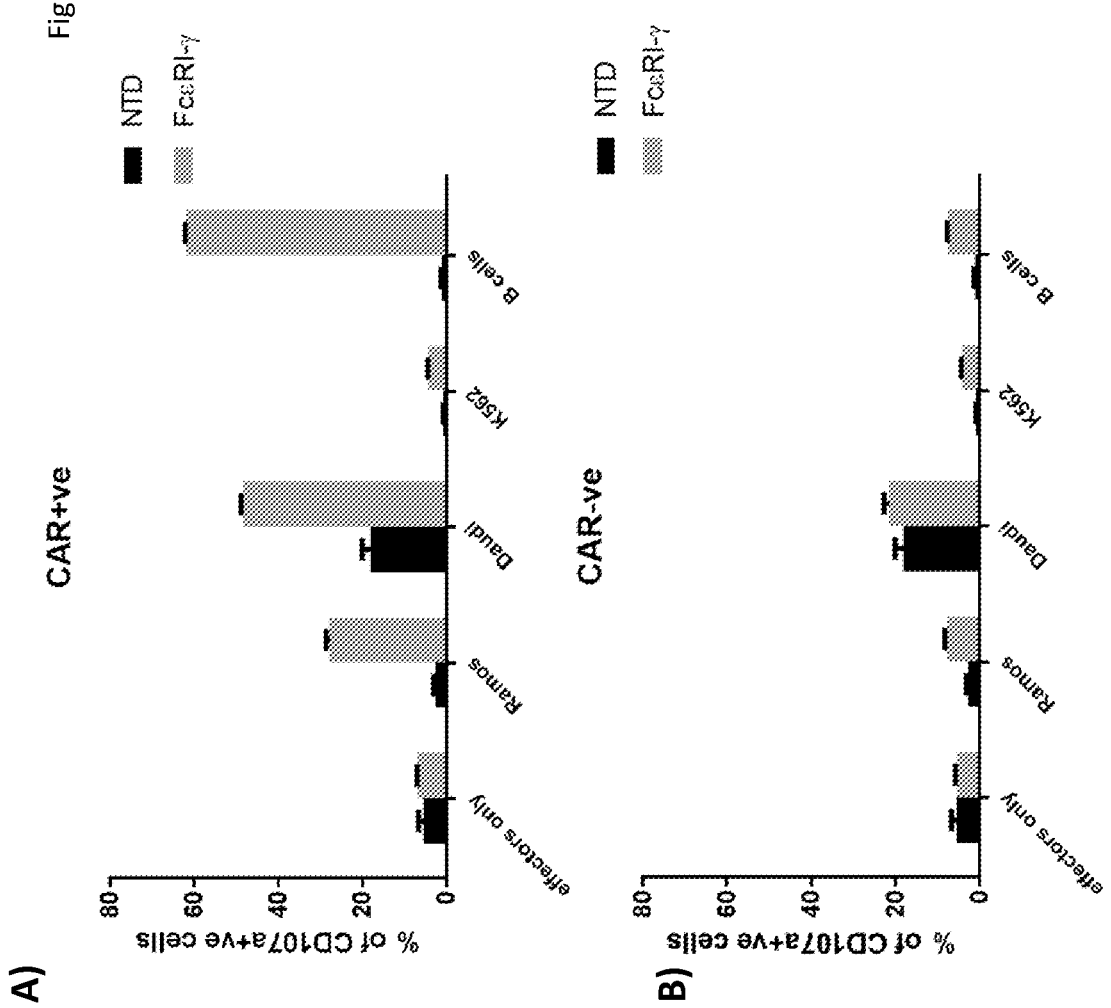

FIG. 6 illustrates Gamma delta T cells transduced to express a CAR comprising of an anti-CD19 scFv, a CD28 stock and transmembrane region and a FcεRI-γ signalling endodomain as depicted in FIG. 4. The cells were co-incubated with CD19 positive Ramos and Daudi cancer cells, CD19 negative K562 cancer cells and CD19 positive healthy B cells at 1:1 ratio. CD107a expression was measured by flow cytometry as a marker of degranulation in the CAR positive (A) and CAR negative (B) gamma delta T cells. Degranulation was significantly increased in the CAR positive gamma delta T cells when co-incubated with CD19 positive cancer cells or B cells but not with CD19 negative cancer cells.

Figure 7:
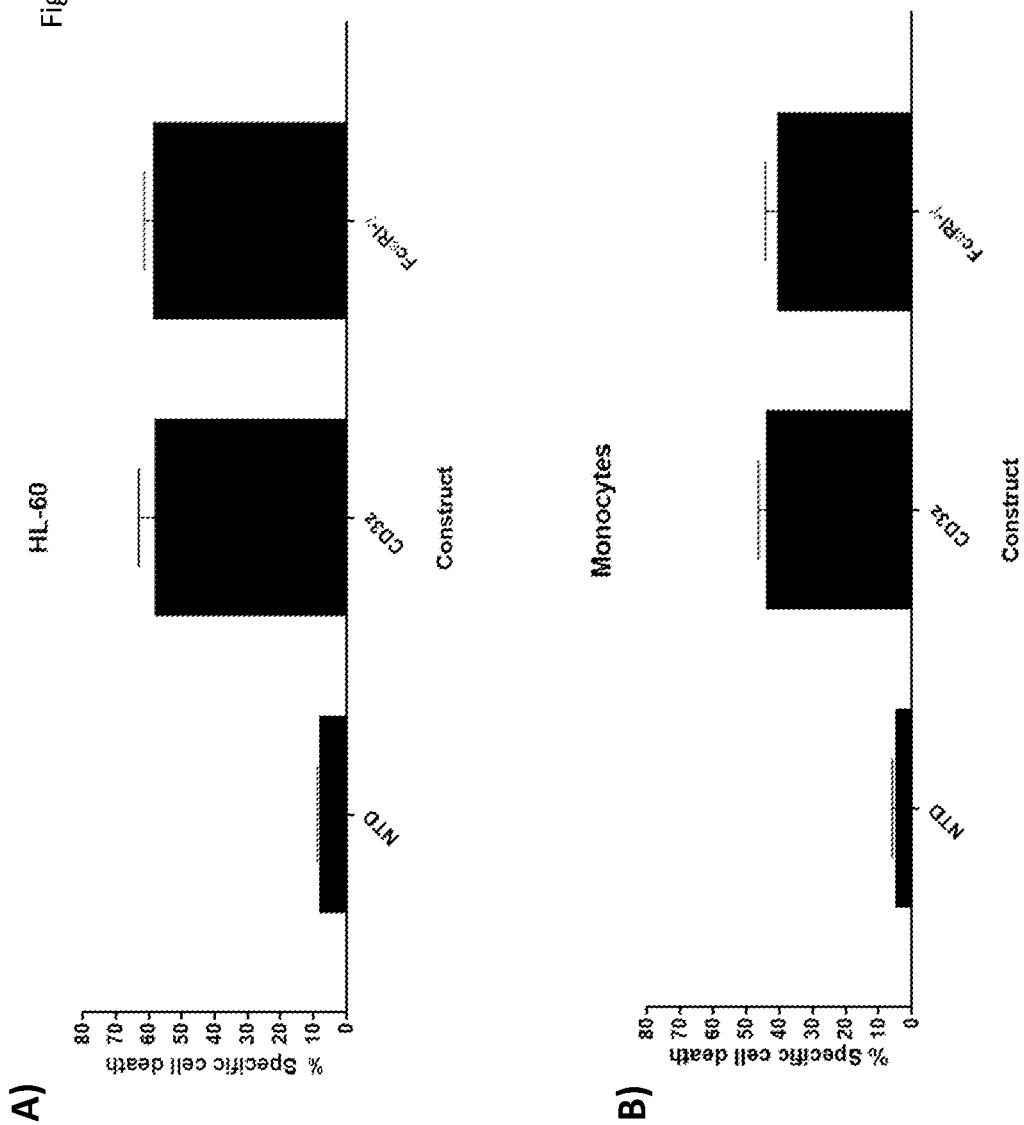

FIG. 7 illustrates Gamma delta T cells transduced to express a CAR comprising of an anti-CD33 scFv, an IgG1 Fc hinge, a CD28 transmembrane region and either a FcεRI-γ or CD3z signalling endodomain as depicted in FIG. 4. The cells were co-incubated with CD33 HL-60 cancer cells or CD33 positive healthy monocytes at 10:1 ratio and their cytotoxic ability was assessed by flow cytometry based on Annexin V and PI staining. Against CD33 positive cancer cells or monocytes, FcεRI-γ and CD3z endodomain containing CARs have equivalent cytotoxicity.

Figure 8:
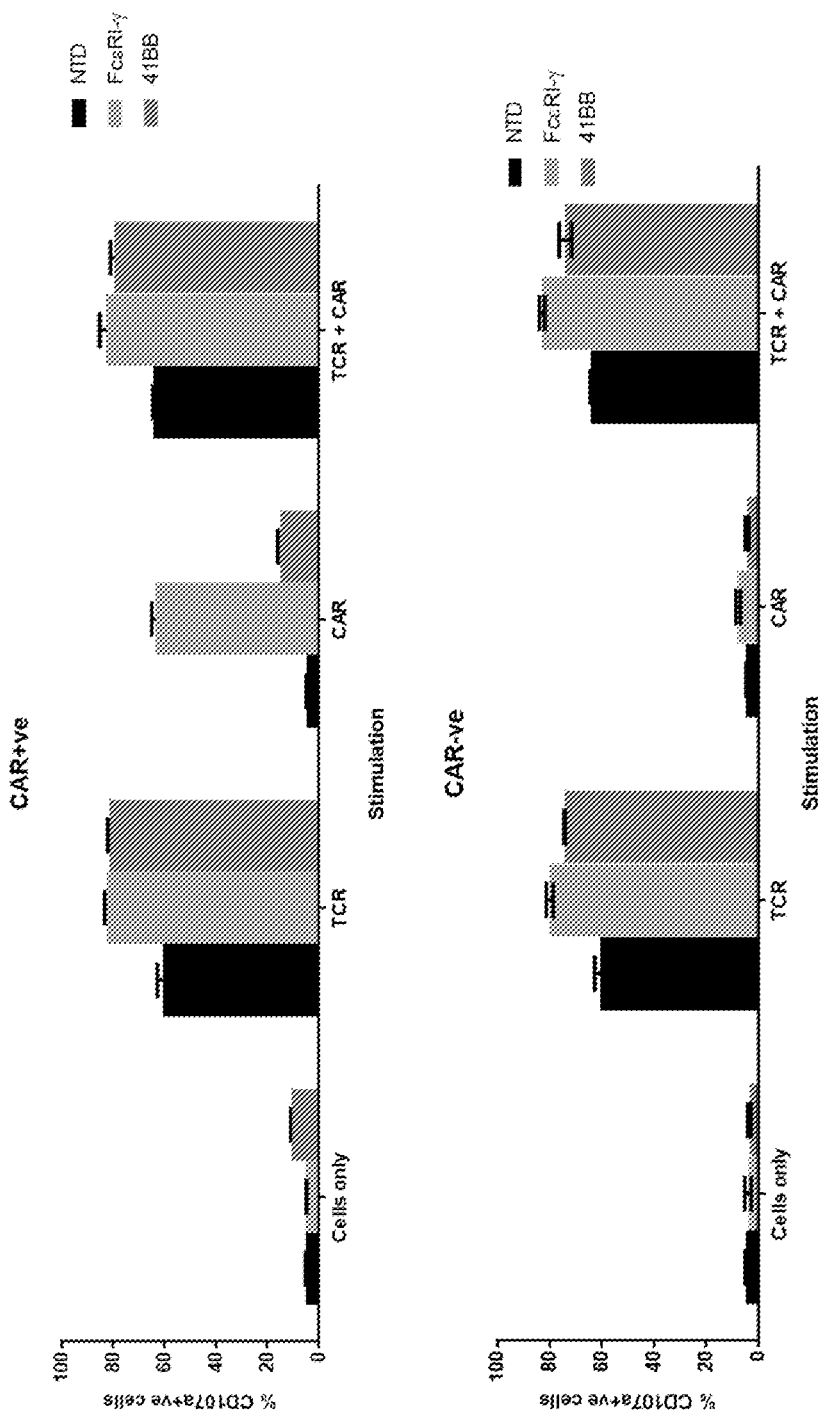

FIG. 8 illustrates Gamma delta T cells transduced to express a CAR comprising of an anti-CD33 scFv, an IgG1 Fc hinge, a CD28 transmembrane region and either a FcεRI-γ or 41BB signalling endodomain as depicted in FIG. 4. The cells were then simulated with MACSiBeads coated in either antibodies against the TCR or soluble CD33 to stimulate the CAR or a combination of both. Degranulation was measured via surface CD107a detection by flow cytometry and correlated with CAR positivity or negativity. Stimulation through the CAR alone causes degranulation where the CAR contains a FcεRI-= but not a 41BB endodomain.

EXAMPLES

Example 1

Generation of a Vector to Allow Transfection of a Gamma Delta T Cells and NK Cells DNA encoding a CD19 targeting CAR encoding for the GMCSF-receptor secretion signal, FMC63 derived scFv, CD28 hinge and transmembrane domain and CD32c activating domain was produced in the pDONR221 backbone between attL1 and attL2 recombination sites.

Example 2

Transduction of Gamma Delta T Cells Using Lentivirus

PBMCs were isolated by density centrifugation (lymphoprep) from leukapheresis material and cryopreserved. PBMCs were resuscitated and zoledronic acid (5 µM) stimulated PBMCs were cultured in the presence of IL-2 (1000 IU/mL) and 5% human AB serum in growth media. After 24 hrs hours in culture (37° C., 5% $CO_2$, humidified atmosphere), cells were transduced with lentivirus with a CD19 targeting CAR incorporating the activation domain of CD32c (as in FIG. 1C). The cells were cultured in G-REX100 cultures flasks for 10 days after transduction and the expression of the CAR was assessed by flow cytometry with an antibody against the extracellular part of the CAR.

Example 3

Transduction of NK Using Lentivirus

PBMCs were isolated by density centrifugation (lymphoprep) from leukapheresis material. CD3+ cells were depleted using MACS. CD3 depleted PBMCs were cultured in the presence of IL-2 (1000 IU/mL) and IL-15 (10-100 ng/ml) and 5% human AB serum in cell culture medium. After 24 hrs to 72 hours in culture (37° C., 5% $CO_2$, humidified atmosphere), cells were transduced with lentivirus with a CD19 targeting CAR incorporating the activation domain of CD32c (as in FIG. 1C). The cells were cultured in G-REX100 cultures flasks for 10 days after transduction and the expression of the CAR was assessed by flow cytometry with an antibody against the extracellular part of the CAR.

Example 4

Using a Transposon Based System for Transfection of Gamma Delta T Cells

The CAR construct in example 1 was cloned into the PB51× vector (System Bioscience). T cells were co-transfected with the PB51× vector and the 'Super' PiggyBac transposase expression vector (System Bioscience) by either Nucleofection (Lonza) or the Neon electroporation system (Thermo Fisher).

Example 5

Demonstration of Increased Cytotoxic Potential of CAR-Expressing Gamma Delta T Cells Gamma delta T cells were transduced to express a CAR consisting of an anti-CD19 scFv, a CD28 stock and transmembrane region and a Fcγ signalling endodomain. The gamma delta T cells were expanded and CAR expression was investigated by flow cytometry.

CAR transduced and non-transduced cells were cocultured with the Burkitt's lymphoma cell line at a 10:1 ratio and their cytotoxic ability was assessed by flow cytometry based on Annexin V and PI staining. Results are illustrated by FIG. 3 and show that CAR-transduced gamma delta T cells exhibited almost twofold cytotoxic capacity compared with non-transduced (control) gamma delta T cells.

Further, as indicated by FIG. 4, co-incubation of the gamma delta T cells transduced to express a CAR comprising of an anti-CD19 scFv, a CD28 stalk and transmembrane region and a FcεRI-γ signalling endodomain with CD19 positive Ramos and Daudi cancer cells, CD19 negative K562 cancer cells and CD19 positive healthy B cells at 10:1 ratio indicated that CAR-transduced gamma delta T cells exhibited significant additional cytotoxicity against CD19 positive cells but not against the CD19 negative K562 cells.

By considering FIG. 5, it is clear that CAR—induced transduced gamma delta T cells as compared to non-transduced (control) gamma delta T cells (wherein the gamma delta T cells are transduced to express a CAR comprising of an anti-CD19 scFv, a CD28 stalk and transmembrane region and a FcεRI-γ signalling endodomain) exhibited significant additional cytotoxicity against CD19 positive cells but not against the CD19 negative K562 cells as compared to non-transduced (control) gamma delta T cells.

Various modifications and variations of the described methods and system of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology, immunology or related fields are intended to be within the scope of the following claims.

The invention claimed is:

1. A gamma delta T cell comprising a nucleic acid construct to provide for expression of a CAR comprising:
   (i) an antigen-binding domain coupled to a trans-membrane domain, and
   (ii) an intracellular activation signalling domain
wherein the intracellular signalling domain consists of one or more Fcγ Receptor intracellular signalling domains, wherein the one or more Fcγ Receptor intracellular signalling domains is from an Fc R common gamma chain, a CD16, a CD32a, a CD32c, or a CD64, and wherein binding of antigen to the antigen binding domain of the CAR causes signalling by the intracellular signalling domain of the CAR.

2. The gamma delta T cell of claim 1, wherein binding by the gamma delta T cell receptor of the gamma delta T cell to a target ligand to which the gamma delta T cell receptor has binding specificity causes a first intracellular signal and binding of the CAR antigen binding domain to a target ligand to which the CAR has binding specificity causes a second intracellular signal, wherein the first and second intracellular signals alone or in combination cause activation of the gamma delta T cell.

3. The gamma delta T cell of claim 1, wherein activation of the gamma delta T cell by a target cell causes activation of the gamma delta T cell to promote cell death of the target cell.

4. The gamma delta T cell of claim 1, comprising a nucleic acid construct encoding a CAR wherein the nucleic acid construct encodes an amino acid sequence selected from at least one of SEQ ID NO:4, SEQ ID NO:5, SEQ ID NO: 6, SEQ ID NO:7, or a combination thereof.

5. The gamma delta T cell of claim 1 wherein:
   (a) the one or more Fcγ Receptor intracellular signalling domains comprises at least one CD32a or CD32c or CD 64 signalling domain, such that binding of antigen to the antigen binding domain of the CAR causes signalling by the intracellular signalling domain of the CAR;
   (b) the CD32a or CD32c signalling domains have a sequence identity of at least 95% to SEQ ID NO 2 or SEQ ID NO: 3; or
   (c) the CAR comprises the amino acid sequence of SEQ ID NO: 6 or SEQ ID NO:7.

6. A pharmaceutical composition comprising a plurality of cells according to claim 1.

7. A pharmaceutical composition comprising a plurality of cells according to claim 1.

\* \* \* \* \*

```
                        SEQUENCE LISTING

<160> NUMBER OF SEQ ID NOS: 15

<210> SEQ ID NO 1
<211> LENGTH: 86
<212> TYPE: PRT
<213> ORGANISM: Artificial Sequence
<220> FEATURE:
<223> OTHER INFORMATION: FcR gamma chain

<400> SEQUENCE: 1

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 2
<211> LENGTH: 317
<212> TYPE: PRT
<213> ORGANISM: Artificial Sequence
<220> FEATURE:
<223> OTHER INFORMATION: CD32a (FCGR2A)

<400> SEQUENCE: 2

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
            85                  90                  95

Asn Asp Ser Gly Glu Tyr Thr Cys Gln Thr Gly Gln Thr Ser Leu Ser
        100                 105                 110

Asp Pro Val His Leu Thr Val Leu Ser Glu Trp Leu Val Leu Gln Thr
    115                 120                 125

Pro His Leu Glu Phe Gln Glu Gly Glu Thr Ile Met Leu Arg Cys His
130                 135                 140

Ser Trp Lys Asp Lys Pro Leu Val Lys Val Thr Phe Phe Gln Asn Gly
```

```
                145                 150                 155                 160
Lys Ser Gln Lys Phe Ser His Leu Asp Pro Thr Phe Ser Ile Pro Gln
                    165                 170                 175
Ala Asn His Ser His Ser Gly Asp Tyr His Cys Thr Gly Asn Ile Gly
                    180                 185                 190
Tyr Thr Leu Phe Ser Ser Lys Pro Val Thr Ile Thr Val Gln Val Pro
                    195                 200                 205
Ser Met Gly Ser Ser Ser Pro Met Gly Ile Ile Val Ala Val Val Ile
                    210                 215                 220
Ala Thr Ala Val Ala Ala Ile Val Ala Ala Val Val Ala Leu Ile Tyr
225                 230                 235                 240
Cys Arg Lys Lys Arg Ile Ser Ala Asn Ser Thr Asp Pro Val Lys Ala
                    245                 250                 255
Ala Gln Phe Glu Pro Pro Gly Arg Gln Met Ile Ala Ile Arg Lys Arg
                    260                 265                 270
Gln Leu Glu Glu Thr Asn Asn Asp Tyr Glu Thr Ala Asp Gly Gly Tyr
                    275                 280                 285
Met Thr Leu Asn Pro Arg Ala Pro Thr Asp Asp Lys Asn Ile Tyr
                    290                 295                 300
Leu Thr Leu Pro Pro Asn Asp His Val Asn Ser Asn Asn
305                 310                 315
```

<210> SEQ ID NO 3
<211> LENGTH: 323
<212> TYPE: PRT
<213> ORGANISM: Artificial Sequence
<220> FEATURE:
<223> OTHER INFORMATION: CD32c (FCGR2C)

<400> SEQUENCE: 3

```
Met Gly Ile Leu Ser Phe Leu Pro Val Leu Ala Thr Glu Ser Asp Trp
1               5                   10                  15
Ala Asp Cys Lys Ser Pro Gln Pro Trp Gly His Met Leu Leu Trp Thr
                    20                  25                  30
Ala Val Leu Phe Leu Ala Pro Val Ala Gly Thr Pro Ala Ala Pro Pro
                    35                  40                  45
Lys Ala Val Leu Lys Leu Glu Pro Gln Trp Ile Asn Val Leu Gln Glu
                    50                  55                  60
Asp Ser Val Thr Leu Thr Cys Arg Gly Thr His Ser Pro Glu Ser Asp
65                  70                  75                  80
Ser Ile Gln Trp Phe His Asn Gly Asn Leu Ile Pro Thr His Thr Gln
                    85                  90                  95
Pro Ser Tyr Arg Phe Lys Ala Asn Asn Asn Asp Ser Gly Glu Tyr Thr
                    100                 105                 110
Cys Gln Thr Gly Gln Thr Ser Leu Ser Asp Pro Val His Leu Thr Val
                    115                 120                 125
Leu Ser Glu Trp Leu Val Leu Gln Thr Pro His Leu Glu Phe Gln Glu
                    130                 135                 140
Gly Glu Thr Ile Val Leu Arg Cys His Ser Trp Lys Asp Lys Pro Leu
145                 150                 155                 160
Val Lys Val Thr Phe Phe Gln Asn Gly Lys Ser Lys Lys Phe Ser Arg
                    165                 170                 175
Ser Asp Pro Asn Phe Ser Ile Pro Gln Ala Asn His Ser His Ser Gly
                    180                 185                 190
Asp Tyr His Cys Thr Gly Asn Ile Gly Tyr Thr Leu Tyr Ser Ser Lys
```

```
                195                 200                 205
Pro Val Thr Ile Thr Val Gln Ala Pro Ser Ser Pro Met Gly Ile
        210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Ser
                245                 250                 255

Thr Asp Pro Val Lys Ala Ala Gln Phe Glu Pro Pro Gly Arg Gln Met
            260                 265                 270

Ile Ala Ile Arg Lys Arg Gln Pro Glu Glu Thr Asn Asn Asp Tyr Glu
        275                 280                 285

Thr Ala Asp Gly Gly Tyr Met Thr Leu Asn Pro Arg Ala Pro Thr Asp
    290                 295                 300

Asp Asp Lys Asn Ile Tyr Leu Thr Leu Pro Pro Asn Asp His Val Asn
305                 310                 315                 320

Ser Asn Asn

<210> SEQ ID NO 4
<211> LENGTH: 391
<212> TYPE: PRT
<213> ORGANISM: Artificial Sequence
<220> FEATURE:
<223> OTHER INFORMATION: (CD19scFv-linker-myc-CD28[EX]-FcR gamma[TM-IN])

<400> SEQUENCE: 4

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240
```

```
Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ser Gly
            260                 265                 270

Gly Gly Gly Ser Glu Gln Lys Leu Ile Ser Glu Glu Asp Leu Ile Glu
        275                 280                 285

Val Met Tyr Pro Pro Pro Tyr Leu Asp Asn Glu Lys Ser Asn Gly Thr
290                 295                 300

Ile Ile His Val Lys Gly Lys His Leu Cys Pro Ser Pro Leu Phe Pro
305                 310                 315                 320

Gly Pro Ser Lys Pro Leu Cys Tyr Ile Leu Asp Ala Ile Leu Phe Leu
                325                 330                 335

Tyr Gly Ile Val Leu Thr Leu Leu Tyr Cys Arg Leu Lys Ile Gln Val
            340                 345                 350

Arg Lys Ala Ala Ile Thr Ser Tyr Glu Lys Ser Asp Gly Val Tyr Thr
        355                 360                 365

Gly Leu Ser Thr Arg Asn Gln Glu Thr Tyr Glu Thr Leu Lys His Glu
    370                 375                 380

Lys Pro Pro Gln Ala Ala Ala
385                 390

<210> SEQ ID NO 5
<211> LENGTH: 394
<212> TYPE: PRT
<213> ORGANISM: Artificial Sequence
<220> FEATURE:
<223> OTHER INFORMATION: (CD19scFv-linker-myc-CD28[EX-TM]-FcR gamma[IN])

<400> SEQUENCE: 5

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205
```

Ala Leu Lys Ser Arg Leu Thr Ile Ile Lys Asp Asn Ser Lys Ser Gln
             210                 215                 220
Val Phe Leu Lys Met Asn Ser Leu Gln Thr Asp Asp Thr Ala Ile Tyr
225                 230                 235                 240
Tyr Cys Ala Lys His Tyr Tyr Tyr Gly Gly Ser Tyr Ala Met Asp Tyr
                 245                 250                 255
Trp Gly Gln Gly Thr Ser Val Thr Val Ser Ser Ala Ala Ala Ser Gly
                 260                 265                 270
Gly Gly Gly Ser Glu Gln Lys Leu Ile Ser Glu Glu Asp Leu Ile Glu
             275                 280                 285
Val Met Tyr Pro Pro Pro Tyr Leu Asp Asn Glu Lys Ser Asn Gly Thr
290                 295                 300
Ile Ile His Val Lys Gly Lys His Leu Cys Pro Ser Pro Leu Phe Pro
305                 310                 315                 320
Gly Pro Ser Lys Pro Phe Trp Val Leu Val Val Val Gly Gly Val Leu
                 325                 330                 335
Ala Cys Tyr Ser Leu Leu Val Thr Val Ala Phe Ile Ile Phe Trp Val
                 340                 345                 350
Arg Leu Lys Ile Gln Val Arg Lys Ala Ala Ile Thr Ser Tyr Glu Lys
             355                 360                 365
Ser Asp Gly Val Tyr Thr Gly Leu Ser Thr Arg Asn Gln Glu Thr Tyr
370                 375                 380
Glu Thr Leu Lys His Glu Lys Pro Pro Gln
385                 390

<210> SEQ ID NO 6
<211> LENGTH: 429
<212> TYPE: PRT
<213> ORGANISM: Artificial Sequence
<220> FEATURE:
<223> OTHER INFORMATION: (CD19scFv-linker-myc-CD28[EX-TM]-CD32a[IN])

<400> SEQUENCE: 6

Met Leu Leu Leu Val Thr Ser Leu Leu Leu Cys Glu Leu Pro His Pro
1               5                   10                  15
Ala Phe Leu Leu Ile Pro Asp Ile Gln Met Thr Gln Thr Thr Ser Ser
                20                  25                  30
Leu Ser Ala Ser Leu Gly Asp Arg Val Thr Ile Ser Cys Arg Ala Ser
             35                  40                  45
Gln Asp Ile Ser Lys Tyr Leu Asn Trp Tyr Gln Gln Lys Pro Asp Gly
50                  55                  60
Thr Val Lys Leu Leu Ile Tyr His Thr Ser Arg Leu His Ser Gly Val
65                  70                  75                  80
Pro Ser Arg Phe Ser Gly Ser Gly Ser Gly Thr Asp Tyr Ser Leu Thr
                 85                  90                  95
Ile Ser Asn Leu Glu Gln Glu Asp Ile Ala Thr Tyr Phe Cys Gln Gln
                 100                 105                 110
Gly Asn Thr Leu Pro Tyr Thr Phe Gly Gly Gly Thr Lys Leu Glu Ile
             115                 120                 125
Thr Gly Ser Thr Ser Gly Ser Gly Lys Pro Gly Ser Gly Glu Gly Ser
             130                 135                 140
Thr Lys Gly Glu Val Lys Leu Gln Glu Ser Gly Pro Gly Leu Val Ala
145                 150                 155                 160
Pro Ser Gln Ser Leu Ser Val Thr Cys Thr Val Ser Gly Val Ser Leu
                 165                 170                 175

-continued

```
Pro Asp Tyr Gly Val Ser Trp Ile Arg Gln Pro Pro Arg Lys Gly Leu
                180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
        210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ser Gly
                260                 265                 270

Gly Gly Gly Ser Glu Gln Lys Leu Ile Ser Glu Glu Asp Leu Ile Glu
            275                 280                 285

Val Met Tyr Pro Pro Pro Tyr Leu Asp Asn Glu Lys Ser Asn Gly Thr
290                 295                 300

Ile Ile His Val Lys Gly Lys His Leu Cys Pro Ser Pro Leu Phe Pro
305                 310                 315                 320

Gly Pro Ser Lys Pro Phe Trp Val Leu Val Val Val Gly Gly Val Leu
                325                 330                 335

Ala Cys Tyr Ser Leu Leu Val Thr Val Ala Phe Ile Ile Phe Trp Val
                340                 345                 350

Cys Arg Lys Lys Arg Ile Ser Ala Asn Ser Thr Asp Pro Val Lys Ala
                355                 360                 365

Ala Gln Phe Glu Pro Pro Gly Arg Gln Met Ile Ala Ile Arg Lys Arg
        370                 375                 380

Gln Leu Glu Glu Thr Asn Asn Asp Tyr Glu Thr Ala Asp Gly Gly Tyr
385                 390                 395                 400

Met Thr Leu Asn Pro Arg Ala Pro Thr Asp Asp Asp Lys Asn Ile Tyr
                405                 410                 415

Leu Thr Leu Pro Pro Asn Asp His Val Asn Ser Asn Asn
                420                 425
```

<210> SEQ ID NO 7
<211> LENGTH: 429
<212> TYPE: PRT
<213> ORGANISM: Artificial Sequence
<220> FEATURE:
<223> OTHER INFORMATION: (CD19scFv-linker-myc-CD28[EX-TM]-CD32c[IN])

<400> SEQUENCE: 7

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
                100                 105                 110
```

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
        130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ala Ser Gly
            260                 265                 270

Gly Gly Gly Ser Glu Gln Lys Leu Ile Ser Glu Glu Asp Leu Ile Glu
        275                 280                 285

Val Met Tyr Pro Pro Pro Tyr Leu Asp Asn Glu Lys Ser Asn Gly Thr
290                 295                 300

Ile Ile His Val Lys Gly Lys His Leu Cys Pro Ser Pro Leu Phe Pro
305                 310                 315                 320

Gly Pro Ser Lys Pro Phe Trp Val Leu Val Val Val Gly Gly Val Leu
                325                 330                 335

Ala Cys Tyr Ser Leu Leu Val Thr Val Ala Phe Ile Ile Phe Trp Val
            340                 345                 350

Cys Arg Lys Lys Arg Ile Ser Ala Asn Ser Thr Asp Pro Val Lys Ala
        355                 360                 365

Ala Gln Phe Glu Pro Pro Gly Arg Gln Met Ile Ala Ile Arg Lys Arg
    370                 375                 380

Gln Pro Glu Glu Thr Asn Asn Asp Tyr Glu Thr Ala Asp Gly Gly Tyr
385                 390                 395                 400

Met Thr Leu Asn Pro Arg Ala Pro Thr Asp Asp Asp Lys Asn Ile Tyr
                405                 410                 415

Leu Thr Leu Pro Pro Asn Asp His Val Asn Ser Asn Asn
            420                 425

<210> SEQ ID NO 8
<211> LENGTH: 232
<212> TYPE: PRT
<213> ORGANISM: Artificial Sequence
<220> FEATURE:
<223> OTHER INFORMATION: hinge-CH2CH3 of human lgG1

<400> SEQUENCE: 8

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Trp Val
        35                  40                  45

-continued

Asp Val Ser His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Trp Ser Val Leu Thr Val Leu His Gln Asp Trp
                 85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
            210                 215                 220

Ser Leu Ser Pro Gly Lys Lys Asp
225                 230

<210> SEQ ID NO 9
<211> LENGTH: 46
<212> TYPE: PRT
<213> ORGANISM: Artificial Sequence
<220> FEATURE:
<223> OTHER INFORMATION: human CD8 stalk

<400> SEQUENCE: 9

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 10
<211> LENGTH: 20
<212> TYPE: PRT
<213> ORGANISM: Artificial Sequence
<220> FEATURE:
<223> OTHER INFORMATION: human IgG1 hinge

<400> SEQUENCE: 10

Ala Glu Pro Lys Ser Pro Asp Lys Thr His Thr Cys Pro Pro Cys Pro
 1               5                  10                  15

Lys Asp Pro Lys
            20

<210> SEQ ID NO 11
<211> LENGTH: 185
<212> TYPE: PRT
<213> ORGANISM: Artificial Sequence
<220> FEATURE:
<223> OTHER INFORMATION: CD2 ectodomain

<400> SEQUENCE: 11

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Ile Asp Asp
            20                  25                  30

Ile Lys Trp Glu Lys Thr Ser Asp Lys Lys Ile Ala Gln Phe Arg
        35                  40                  45

Lys Glu Lys Glu Thr Phe Lys Glu Lys Asp Thr Tyr Lys Leu Phe Lys
50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185

<210> SEQ ID NO 12
<211> LENGTH: 259
<212> TYPE: PRT
<213> ORGANISM: Artificial Sequence
<220> FEATURE:
<223> OTHER INFORMATION: CD34 ectodomain

<400> SEQUENCE: 12

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

Pro Ser Thr Leu Gly Ser Thr Ser Leu His Pro Val Ser Gln His Gly
        35                  40                  45

Asn Glu Ala Thr Thr Asn Ile Thr Glu Thr Thr Val Lys Phe Thr Ser
50                  55                  60

Thr Ser Val Ile Thr Ser Val Tyr Gly Asn Thr Asn Ser Ser Val Gln
65                  70                  75                  80

Ser Gln Thr Ser Val Ile Ser Thr Val Phe Thr Thr Pro Ala Asn Val
                85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
        115                 120                 125

Pro Tyr Thr Ser Ser Ser Pro Ile Leu Ser Asp Ile Lys Ala Glu Ile
130                 135                 140

Lys Cys Ser Gly Ile Arg Glu Val Lys Leu Thr Gln Gly Ile Cys Leu
145                 150                 155                 160

```
Glu Gln Asn Lys Thr Ser Ser Cys Ala Glu Phe Lys Lys Asp Arg Gly
                165                 170                 175

Glu Gly Leu Ala Arg Val Leu Cys Gly Glu Gln Ala Asp Ala Asp
            180                 185                 190

Ala Gly Ala Gln Val Cys Ser Leu Leu Leu Ala Gln Ser Glu Val Arg
        195                 200                 205

Pro Gln Cys Leu Leu Leu Val Leu Ala Asn Arg Thr Glu Ile Ser Ser
    210                 215                 220

Lys Leu Gln Leu Met Lys Lys His Gln Ser Asp Leu Lys Leu Gly
225                 230                 235                 240

Ile Leu Asp Phe Thr Glu Gln Asp Val Ala Ser His Gln Ser Tyr Ser
                245                 250                 255

Gln Lys Thr

<210> SEQ ID NO 13
<211> LENGTH: 39
<212> TYPE: PRT
<213> ORGANISM: Artificial Sequence
<220> FEATURE:
<223> OTHER INFORMATION: human CD28 stalk

<400> SEQUENCE: 13

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 14
<211> LENGTH: 6
<212> TYPE: PRT
<213> ORGANISM: Artificial Sequence
<220> FEATURE:
<223> OTHER INFORMATION: SGGGS linker

<400> SEQUENCE: 14

Ser Gly Gly Gly Gly Ser
1               5

<210> SEQ ID NO 15
<211> LENGTH: 10
<212> TYPE: PRT
<213> ORGANISM: Artificial Sequence
<220> FEATURE:
<223> OTHER INFORMATION: myc tag

<400> SEQUENCE: 15

Glu Gln Lys Leu Ile Ser Glu Glu Asp Leu
1               5                   10
```